(12) United States Patent
Cruz

(10) Patent No.: US 7,803,766 B2
(45) Date of Patent: Sep. 28, 2010

(54) GASTRIN COMPOSITIONS AND FORMULATIONS, AND METHODS OF USE AND PREPARATION

(75) Inventor: Antonio Cruz, Toronto (CA)

(73) Assignee: Warath Pharmaceuticals, Inc, Toronto, Ontario (CA)

( * ) Notice: Subject to any disclaimer, the term of this patent is extended or adjusted under 35 U.S.C. 154(b) by 551 days.

(21) Appl. No.: 11/701,196

(22) Filed: Jan. 31, 2007

(65) Prior Publication Data

US 2009/0075873 A1 Mar. 19, 2009

Related U.S. Application Data

(63) Continuation of application No. 10/535,745, filed as application No. PCT/CA2003/001778 on Nov. 21, 2003, now abandoned.

(60) Provisional application No. 60/428,100, filed on Nov. 21, 2002, provisional application No. 60/428,562, filed on Nov. 22, 2002, provisional application No. 60/430,590, filed on Dec. 3, 2002, provisional application No. 60/519,933, filed on Nov. 14, 2003.

(51) Int. Cl.
*A61K 38/16* (2006.01)
*C07K 14/00* (2006.01)

(52) U.S. Cl. ........................ 514/12; 530/309; 530/363

(58) Field of Classification Search ................ None
See application file for complete search history.

(56) References Cited

U.S. PATENT DOCUMENTS

| | | | |
|---|---|---|---|
| 4,464,363 A | 8/1984 | Higuchi et al. | 424/232 |
| 4,686,283 A | 8/1987 | Nestor, Jr. et al. | |
| 4,760,023 A | 7/1988 | Miyoshi et al. | |
| 4,997,950 A | 3/1991 | Murphy et al. | |
| 5,023,077 A | 6/1991 | Gevas et al. | 424/88 |
| 5,041,533 A | 8/1991 | Wunsch et al. | |
| 5,166,322 A | 11/1992 | Shaw et al. | |
| 5,189,049 A | 2/1993 | Frehel et al. | 514/371 |
| 5,506,107 A | 4/1996 | Cunningham et al. | |
| 5,837,460 A | 11/1998 | Von Feldt et al. | |
| 5,885,956 A | 3/1999 | Nardi et al. | |
| 6,150,327 A | 11/2000 | Sinn et al. | 514/8 |
| 6,267,964 B1 | 7/2001 | Nygren et al. | |
| 6,288,301 B1 | 9/2001 | Nardi et al. | |
| 6,423,685 B1 | 7/2002 | Drummond et al. | 514/12 |
| 6,558,952 B1 | 5/2003 | Parikh et al. | |
| 6,593,295 B2 | 7/2003 | Bridon et al. | 514/2 |
| 6,686,179 B2 | 2/2004 | Fleer et al. | |
| 6,899,883 B2 | 5/2005 | Dupre | |
| 6,989,148 B2 | 1/2006 | Dupre | |
| 6,992,060 B2 | 1/2006 | Brand | |
| 7,037,504 B2 | 5/2006 | Magil et al. | |
| 2002/0072115 A1 | 6/2002 | Harrison et al. | |
| 2002/0081285 A1 | 6/2002 | Parikh et al. | |
| 2002/0119146 A1 | 8/2002 | Dupre | 424/139.1 |
| 2002/0182728 A1 | 12/2002 | Ramiya et al. | 435/366 |
| 2004/0023885 A1 | 2/2004 | Brand et al. | |
| 2004/0037818 A1 | 2/2004 | Brand et al. | |
| 2004/0209801 A1 | 10/2004 | Brand et al. | |
| 2004/0209816 A1 | 10/2004 | Parikh et al. | |
| 2004/0229810 A1 | 11/2004 | Cruz | |
| 2004/0266682 A1 | 12/2004 | Cruz | |
| 2006/0183674 A1 | 8/2006 | Brand et al. | |
| 2006/0189520 A1 | 8/2006 | Brand et al. | |
| 2006/0234373 A1 | 10/2006 | Rabinovitch et al. | |
| 2006/0234932 A1 | 10/2006 | Brand | |

FOREIGN PATENT DOCUMENTS

| | | |
|---|---|---|
| CN | 1169827 C | 10/2004 |
| EP | 0 380 230 A2 | 8/1990 |
| WO | WO-9012874 A2 | 11/1990 |
| WO | WO-9101743 A1 | 2/1991 |
| WO | WO 93/03757 | 3/1993 |
| WO | WO 95/19785 | 7/1995 |
| WO | WO 95/31214 | 11/1995 |
| WO | WO 00/29438 | 5/2000 |
| WO | WO 00/44400 | 8/2000 |
| WO | WO 01/39784 A1 | 6/2001 |

(Continued)

OTHER PUBLICATIONS

K.H. Welch et al. Z. Gastroenterologie (1971) 9, pp. 185-194.*

(Continued)

*Primary Examiner*—Andrew D Kosar
(74) *Attorney, Agent, or Firm*—Mintz Levin Cohn Ferris Glovsky and Popeo, P.C.; Ivor R. Elrifi, Esq.; David E. Johnson, Esq.

English Translation of K. H. Welch et al. Z. Gastroenterologie (1971) 9. 22 pages.*
Ahmed et al., "High and Low Affinity Receptors Mediate Growth Effects of Gastrin and Gastrin-Gly on DLD-1 Human Colonic Carcinoma Cells", *FEBS Letters*, 556:199-203 (2004).
Baggio et al., "Therapeutic approaches to preserve islet mass in type 2 diabetes", *Annual Review of Medicine*, 57:265-281 (2006).
Baldwin et al., "Measurement of Gastrin and Transforming Growth Factor a Messenger RNA Levels in Colonic Carcinoma Cell Lines by Quantitative Polymerase Chain Reaction", *Cancer Research*, 52:2261-2267 (1992).

(57) ABSTRACT

The present invention concerns six novel variants of alternative splicing of the CD40 receptor The invention provides a pharmaceutical composition comprising a gastrin compound having an extended activity upon administration to a subject in comparison with native gastrin. Methods are provided of conjugating portions of the amino acid sequence of gastrin having functional ability to bind to the gastrin/CCK receptor, to various carrier moieties, including the use of amino acid spacer regions, and use of bifunctional cross-linking reagents. Methods of treating a diabetes patient with the compositions are provided.

15 Claims, 1 Drawing Sheet

FOREIGN PATENT DOCUMENTS

| WO | WO 02/10195 A2 | 2/2002 |
|---|---|---|
| WO | WO 02/055152 A2 | 7/2002 |
| WO | WO 03/040310 A2 | 5/2003 |
| WO | WO 03/100024 A2 | 12/2003 |
| WO | WO 03/103701 A1 | 12/2003 |
| WO | WO 2004/037195 A2 | 5/2004 |
| WO | WO 2004/045640 A1 | 6/2004 |
| WO | WO 2004/096853 A1 | 11/2004 |
| WO | WO 2004/105780 A2 | 12/2004 |
| WO | WO 2005/072045 A2 | 8/2005 |
| WO | WO 2006/002532 A1 | 1/2006 |
| WO | WO 2007/041833 A1 | 4/2007 |
| WO | WO 2007/062531 A1 | 6/2007 |
| WO | WO 2007/095737 A1 | 8/2007 |

OTHER PUBLICATIONS

Baldwin, G.S., "The role of gastrin and cholecystokinin in normal and neoplastic gastrointestinal growth", *J. Gastroenterol. Hepatol.*, 10(2):215-232 (1995).

Bentley et al., "Human Gastrin: Isolation, Structure and Synthesis", *Nature*, 209:583-585 (1966).

Bonato et al., "Guinea Pig 33-Amino Acid Gastrin", *Life Science*, 39:959-964 (1986).

Brand et al., "Differential Gastrin Gene Expression in Rat Gastrointestinal Tract and Pancreas during Neonatal Development", *J. Biol. Chem.*, 263(11):5341-5347 (1988).

Brand et al., "Gastrin Gene Expression and Regulation in Rat Islet Cell Lines", *J. Biol. Chem.*, 263:16597-16603 (1994).

Brand et al., "Prolonged Efficacy of Islet Neogenesis Therapy with Gastrin and TGFα in Mature Rats with Preexisting Diabetes", *Diabetes*, 50(Suppl 2):A338 (Abstract) (2001).

Brenna et al., "Trophic effect of gastrin on the enterochromaffin like cells of the rat stomach: establishment of a dose response relationship", *Gut*, 33(10):1303-1306 (1992).

Carlsson et al., "Gastrin and gastric enterochromaffin-like cell carcinoids in the rat", *Digestion*, 47(Suppl 1):17-23, "Discussion", pp. 49-52 (1990).

Chen et al., "Time course of hypertrophic and ultrastructural responses of rat stomach enterochromaffin-like cells to sustained hypergastrinemia", *Cell Tissue Res.*, 284(1):55-63 (1994).

Dembinski et al., "Stimulation of Pancreatic Growth by Secretin, Caerulein, and Pentagastrin", *Endocrinology*, 106(1):323-328 (1980).

Drucker, D.J., "Glucagon-Like Peptides: Regulators of Cell Proliferation, Differentiation, and Apoptosis", *Molecular Endocrinology*, 17(2):161-171 (2003).

Dupre et al., "Effects of Secretin, Pancreozymin, or Gastrin on the Response of the Endocrine Pancreas to Administration of Glucose or Arginine in Man", *Journal of Clinical Investigation*, 48:745-757 (1969).

Durrant et al., "Co-stimulation of Gastrointestinal Tumour Cell Growth by Gastrin, Transforming Growth Factor α and Insulin Like Growth Factor-1", *Brit. J. Cancer*, 63:67-70 (1991).

Elder et al., "Effect of urogastrone in the Zollinger-Ellison syndrome", *The Lancet*, 2(7932):424-427 (1975).

Elder et al., "Effect of urogastrone on gastric secretion and plasma gastrin levels in normal subjects", *Gut*, 16(11):887-893 (1975).

Ennis et al., "The EGF receptor system as a target for antitumor therapy", *Cancer Invest.*, 9(5):553-562 (1991).

GenBank Accession No. AAH69762, Jul. 2006.

GenBank Accession No. NP_000796, Nov. 2007.

Gil et al., "Polymeric Biomaterials as Drug Delivery Systems", *Boletim et Biotecnologia*, 72:13-19 (2002).

Han et al., "Altered pharmacokinetics and liver targetability of methotrexate by conjugation with lactosylated albumins", *Drug. Deliv.*, 8(3):125-134 (2001).

Jensen, R.T., "Gastrinoma as a model for prolonged hypergastrinemia in the human", in *Gastrin*, Chapter 29, pp. 373-393, Raven Press Ltd., New York (1993).

Kopin et al., "The role of the cholecystokinin-B/gastrin receptor transmembrane domains in determining affinity for subtype-selective ligands", *J. Biol. Chem.*, 270(10):5019-5023 (1995).

Korc et al., "Regulation of Protein Synthesis in Normal and Diabetic Rat Pancreas by Cholecystokinin", *Am. J. Physiol.*, 241:G116-G121 (1981).

Korc, M.J., "Islet Growth Factors: Curing Diabetes and Preventing Chronic Pancreatitis?", *Clin. Invest.*, 92:1113-1114 (1993).

Kuntz et al., "Cholecystokinin Octapeptide: A Potential Growth Factor for Pancreatic Beta Cells in Diabetic Rats", *Journal of Pancreas*, 5(6):464-475 (2004).

Larsson et al., "Pancreatic gastrin in foetal and neonatal rats", *Nature*, 262:609-610 (1976).

Low et al., "Development of peptide 3D structure mimetics: rational design of novel peptoid cholecystokinin receptor antagonists", *J. Med. Chem.*, 43:3505-3517 (2000).

Sacchi et al., "Nesidioblastosis and Islet Cell Changes Related to Endogenous Hypergastrinemia", *Virchows Archiv. B.* [*Cell Path*], 48:261-276 (1985).

Shu-qi et al., "Chemical Modification of Protein and Biochemical Drugs", *Chinese Journal of Biochemical Pharmaceutics*, 19(5):1-7 (1998).

"SIGMA: Designing Custom Peptides", http://www.sigma-genosys.com/peptide_design.asp, pp. 1-2.

Taylor et al., "Serum gastrin in patients with chronic renal failure", *Gut*, 21(12):1062-1067 (1980).

"Transition Therapeutics Confirms Effectiveness of Islet Neogenesis Therapy in Reducing Diabetic Symptoms", Transition Therapeutics Press Release, Apr. 17, 2002.

"Transition Therapeutics Inc. Receives Approval to Initiate Phase I Clinical Trial for Islet Neogenesis Therapy", Transition Therapeutics Press Release, Sep. 20, 2002.

"Transition Therapeutics' I.N.T.™ Treatment Stimulates Regeneration of Human Insulin-Producing Cells", Transition Therapeutics Press Release, Sep. 26, 2002.

"Transition Therapeutics' I.N.T.™ Treatment Increases Survival", Transition Therapeutics Press Release, Sep. 27, 2002.

Unger et al., "The Effects of Secretin, Pancreozymin, and Gastrin on Insulin and Glucagon Secretion in Anethetized Dogs", *Journal of Clinical Investigation*, 46(4):630-645 (1967).

Von Herrath, M., "E1-INT Transition Therapeutics/Novo Nordisk", *Current Opinion Investig. Drugs*, 6(10):1037-1042 (2005).

Whitaker et al., "Polymeric Delivery of Protein-Based Drugs", *Bus. Brief: Pharmatech*, pp. 1-5 (2002).

Ye et al., "DepoFoam technology: a vehicle for controlled delivery of protein and peptide drugs", *J. Controlled Rel.*, 64:166-166 (2000).

Saillan-Barreau et al., "Evidence for a functional role of the cholecystokinin-B/gastrin receptor in the human fetal and adult pancreas", *Diabetes*, 48:2015-2021 (1999).

Aly et al., "Short term infusion of glycine-extended gastrin$_{17}$ stimulates both proliferation and formation of aberrant crypt foci in rat colonic mucosa", *Int. J. Cancer*, 94:307-313 (2001).

Aly et al., "Gastrins, cholecystokinins and gastrointestinal cancer", *Biochimica et Biophysica Acta*, 1704:1-10 (2004).

Anderson et al., "The human plasma proteome: history, character, adn diagnostic prospects", *Mol. Cell. Proteomics*, 1:845-867 (2002).

Baggio et al., "Sustained expression of exendin-4 does not perturb glucose homeostasis, β-cell mass, or food intake in metallothionein-preproexendin transgenic mice", *J. Biol. Chem.*, 275(44):34471-34477 (2000).

Behr et al., "Radiolabeled peptides for targeting cholecystokinin-B/gastrin receptor-expressing tumors", *J. Nucl. Med.*, 40:1029-1044 (1999).

Boniface et al., "Clearance rate, half-life, and secretory potency of human gastrin-17-I in different species", *Gastroenterol.*, 71:291-294 (1976).

Brelje et al., "The physiological roles of prolactin, growth hormone and placental lactogen in the regulation of islet β cell proliferation", *Pancreatic Growth Regen.*, Chapter 1, pp. 1-30 (1997).

Carlsson et al., "Protein thiolation and reversible protein-protein conjugation", *Biochem. J.*, 173:723-737 (1978).

Carpenter et al., "The epidermal growth factor family", Chapter 4, pp. 69-171 (1990).

Crean et al., "Parietal cell hyperplasia induced by the administration of pentagastrin (ICI 50,123) to rats", *Gastroenterol.*, 57(2):147-155 (1969).

Cunningham et al., "Receptor and antibody Epitopes in human growth hormone identified by homolog-scanning mutagenesis", *Science*, 243:1330-1336 (1989).

Cunningham et al., "High-resolution Epitope mapping of hGH-receptor interactions by alanine-scanning mutagenesis", *Science*, 244:1081-1085 (1989).

Dockray et al., "Immunochemical characterization of gastrin pancreatic islets of normal and genetically obese mice", *J. Endocrinol.*, 72:143-151 (1977).

Dockray et al., "Postsecretory processing of heptadecapeptide gastrin: conversion to C-terminal immunoreactive fragments in the circulation of the dog", *Gastroenterol.*, 83(1):224-232 (1982).

Dockray, G.J., "Topical review. Gastrin and gastric epithelial physiology" *J. Physiol.*, 518(pt.2):315-324 (1999).

Drucker, D.J., "Minireview: the glucagon-like peptides", *Endocrinol.*, 142(2):521-529 (2001).

Elbrønd et al., "Pharmacokinetics, pharmacodynamics, safety, and tolerability of a single-dose of NN2211, a long-acting glucagon-like peptide 1 derivative, in healthy male subjects", *Diabetes Cure*, 25:1398-1404 (2002).

Felix A.M., "Site-specific poly(ethylene glycol)ylation of peptides", *Chemistry and Biological Applications*, Chapter 16, pp. 218-238 (1997).

García-Ocaña et al., "Using β-cell growth factors to enhance human pancreatic islet transplantation", *J. Clin. Endocrinol. Metab.*, 86(3):984-988 (2001).

Goeddel et al., "Direct expression in *Escherichia coli* of a DNA sequence coding for human growth hormone", *Nature*, 281:544-548 (1979).

Gray et al., "Periplasmic production of correctly processed human growth hormone in *Escherichia coli*: natural and bacterial signal sequences are interchangeable", *Gene*, 39:247-254 (1985).

Hughes et al., "NVP-LAF237, a highly selective and long-acting dipeptidyl peptidase IV inhibitor", Abstract 272-OR, p. A67 (2002).

Ito et al., "Structural analysis of the gene encoding human gastrin: the large intron contains an Alu sequence", *Proc. Natl. Acad. Sci. USA*, 81:4662-4666 (1984).

Koffman et al., "Effect of urogastrone on gastric secretion and serum gastrin concentration in patients with duodenal ulceration", *Gut*, 23:951-956 (1982).

Lima-Leite et al., "Synthesis and biological activities of some human gastrin analogs", *Braz. J. Med. Biol. Res.*, 29:1253-1263 (1996).

Lin et al., "A71378: a CCK agonist with high potency and selectivity for CCK-A receptors", *Am. J. Physiol.*, 258(4-pt.1):G648-G651 (1990).

Lin et al., "Introduction of sulfhydryl groups into proteins at carboxyl sites", *Biochimica et Biophysica Acta*, 1038:382-385 (1990).

Mode et al., "The human growth hormone (hGH) antagonist $^{G120R}$hGH does not antagonize GH in the rat, but has paradoxical agonist activity, probably via the prolactin receptor", *Endocrinol.*, 137(2):447-454 (1996).

Nauck et al., "Additive insulinoropic effects of exogenous synthetic human gastric inhibitory polypeptide and glucagon-like peptide-1-(7-36) amide infused at near-physiological insulinotropic hormone and glucose concentrations", *J. Clin. Endocrinol. Metab.*, 76(4):912-917 (1993).

Nielsen et al., "Beta cell proliferation and growth factors", *J. Mol. Med.*, 77:62-66 (1999).

Ørskov et al., "Tissue and plasma concentrations of amidated and glycine-extended glucagon-like peptide I in humans", *Diabetes*, 43:335-339 (1994).

Pedersen et al., "Reactivity of the thiol group in human and bovine albumin at pH 3-9, as measured by exchange with 2,2'-dithiodipyridine", *Eur. J. Biochem.*, 106:291-295 (1980).

Rehfeld et al., "The effect of gastrin on basal- and glucose-stimulated insulin secretion in man", *J. Clin. Invest.*, 52:1415-1426 (1973).

Rehfeld et al., "The effect of gastrin and cholecystokinin on the endocrine pancreases", *Front. Hormone Res.*, 7:107-118 (1980).

Rehfeld, J.F., "The new biology of gastrointestinal hormones", *Physiol. Rev.*, 78(40:1087-1108 (1998).

Rooman et al., "Effects of gastrin on proliferation and differentiation in regenerating pancreas", *Diabetologia*, Abstract, (2000).

Rooman et al., "Gastrin stimulates β-cell neogenesis and increases islet mass from transdifferentiated but not from normal exocrine pancreas tissue", *Diabetes*, 51:686-690 (2002).

Ryberg et al., "Trophic effects on continuous infusion of [Leu$^{15}$]-gastrin-17 in the rat", *Gastroenterol.*, 98:33-38 (1990).

Sandvik et al., "Biological activity of carboxy-terminal gastrin analogs", *Eur. J. Pharmacol.*, 364:199-203 (1999).

Sasaki et al., "Dietary docosahexaenoic acid can alter the surface expression of CD4 and CD8 on T cell in peripheral blood", *J. Agric. Food Chem.*, 48:1047-1049 (2000).

Sigma, "G9145 [Leu$^{15}$]-gastrin I human", http://www.sigmaaldrich.com/catalog/search/ProductDetail/SIGMA/G9145, (2006).

Sigma, "G7264 big gastrin I human", https://www.sigmaaldrich.com/catalog/search/ProductDetail/SIGMA/G7264, (2006).

Slice et al., "Gastrin and EGF synergistically induce cyclooxygenase-2 expression in Swiss 3T3 fibroblasts that express the CCK$_2$ receptor", *J. Cell. Physiol.*, 196:454-463 (2003).

Taylor et al., "Effect of individual $_L$-amino acids on gastric acid secretion and serum gastrin and pancreatic polypeptide release in humans", *Gastroenterol.*, 83:273-278 (1982).

Thanou et al., "Polymer-protein and polymer-drug conjugate in cancer therapy", *Curr. Opin. Investig. Drugs*, 4(6):701-709 (2003).

Tracy et al., "Physiological properties of a series of synthetic peptides structurally related to gastrin 1" *Nature*, 204:935-938 (1964).

Vergelli et al., "Immunosuppressive activity of 13-cis-retinoic acid in rats: aspects of pharmacokinetics and pharmacodynamics", *Immunopharmacol.*, 37:191-197 (1997).

Veronese, F.M., "Peptide and protein PEGylation: a review of problems and solutions", *Biomaterials*, 22:405-417 (2001).

Wang et al., "Function and regulation of gastrin in transgenic mice: a review", *Yale J. Biol. Med.*, 65:705-713 (1992).

Wang et al., "Pancreatic gastrin stimulates islet differentiation of transforming growth factor α-induced ductular precursor cells", *J. Clin. Invest.*, 92:1349-1356 (1993).

Winer et al., "Autoimmune islet destruction in spontaneous type I diabetes is not β-cell exclusive", Nat. Med., 9(2):198-205 (2003).

Yoshitake et al., "Conjugation of glucose oxidase from *Aspergillus niger* and rabbit antibodies using N-hydroxysuccinimide ester of n-(4-carboxycyclohexylmethyl)-maleimide", *Eur. J. Biochem.*, 101:395-399 (1979).

\* cited by examiner

GASTRIN COMPOSITIONS AND FORMULATIONS, AND METHODS OF USE AND PREPARATION

This application is a continuation of U.S. Ser. No. 10/535,745, filed Nov. 17, 2005 now abandoned, which is a National Stage of International Application No. PCT/CA2003/001778, filed Nov. 21, 2003, which claims the benefit of U.S. Ser. No. 60/428,100, filed Nov. 21, 2002, U.S. Ser. No. 60/428,562, filed Nov. 22, 2002, U.S. Ser. No. 60/430,590, filed Dec. 3, 2002, and U.S. Ser. No. 60/519,933, filed Nov. 14, 2003. Priority is claimed to all of these referenced applications. The contents of all of these applications are incorporated by reference in their entireties.

FIELD OF THE INVENTION

The invention in various embodiments provides gastrin compositions having longer active function in vivo than gastrin peptides, and methods of making and using the gastrin compositions for treatment of diabetes.

BACKGROUND OF INVENTION

Therapeutic agents such as peptides and low molecular weight proteins used in the treatment of diseases suffer from significant limitations. These agents are often eliminated by the kidneys within a short period of time or are destroyed by proteases therefore limiting their bioavailability, resulting in short plasma half-life and lower drug concentrations than are required to be efficacious. A high clearance of a therapeutic agent is not optimal in cases where it is desired to maintain a high serum level over an extended period of time to obtain maximal efficacy. Increased doses or increased frequency of administration often result in a higher therapeutic efficacy but a higher risk of side effects as well, limiting the dose or frequency that can be administered.

Many peptide hormones have extremely short half-lives in the bloodstream, resulting in the loss of biological activity not long after administration. Gastrin is a peptide hormone that has been shown in combination with other growth factors to be efficacious in the treatment of diabetes. However, when gastrin is administered alone, there is only limited efficacy. In addition, it has been found that gastrin has a relatively short half life. Gastrin-17 for instance has a circulating half-life of about 5-9 mins while gastrin-34 has a circulating half-life of about 35 mins.

There is a need for compositions containing gastrin compounds that have a protracted or long-acting action.

SUMMARY

A featured embodiment of the invention provides a pharmaceutical composition comprising a gastrin compound having an extended activity upon administration to a subject in comparison with native gastrin. The gastrin component in this embodiment contains at least amino acids selected from the group of: positions 29-34 of SEQ ID NO:1; positions 29-34 of SEQ ID NO:2; positions 12-17 of SEQ ID NO: 3; and positions 12-17 of SEQ ID NO: 4, and the gastrin is further associated with a protein, a polymer, a lipid or a carbohydrate.

An alternative featured embodiment provides a gastrin compound comprising: $Z—Y_m—X_n-AA_1-AA_2-AA_3-AA_4-AA_5-AA_6$, wherein $AA_1$ is Tyr or Phe, $AA_2$ is Gly, Ala, or Ser, $AA_3$ is Trp, Val, or Ile, $AA_4$ is Met or Leu, $AA_5$ is Asp or Glu, and $AA_6$ is Phe or Tyr the $AA_6$ being amidated; wherein Z is a polymer which when the polymer is a protein, Z is the amino acid sequence of the protein; $Y_m$ is an optional spacer region comprising m amino acid residues of a small neutral amino acid, and X is selected from any consecutive portions of: residues 1-28 of SEQ ID NO: 1, residues 1-28 of SEQ ID NO: 2, residues 1-11 of SEQ ID NO: 3, and residues 1-11 of SEQ ID NO: 4, providing that the gastrin compound binds a gastrin/CCK receptor. The $AA_1-AA_2-AA_3-AA_4-AA_5-AA_6$ is, for example, Tyr-Gly-Trp-Met-Asp-Phe. Alternatively, the $AA_1-AA_2-AA_3-AA_4-AA_5-AA_6$ is Tyr-Gly-Trp-Leu-Asp-Phe. In this formula, Z can be a protein, for example, Z is human serum albumin.

$Y_m$ can be an amino acid sequence comprising m residues having glycine alternating with alanine, for example, $[Gly-Ala]_5$, or having random sequence of glycine and alanine. The gastrin compound further can have a cysteine residue at the amino terminus of Y, when m is greater than 1, or at the amino terminus of X, when m is 0. The gastrin compound can further comprise of a bifunctional crosslinking agent for linkage to Z. In general, m is 0 to about 20 residues. In certain embodiments, if m is 0, wherein $X_n-AA_1-AA_2-AA_3-AA_4-AA_5-AA_6$ further comprises a bifunctional cross-linking agent for linkage to Z.

The X in certain embodiments is selected from the group of sequences: position 1 to position 11 of SEQ ID NO: 3; position 1 to position 11 of SEQ ID NO: 4; position 2 to position 11 of SEQ ID NO: 3; and position 2 to position 11 of SEQ ID NO: 4. The gastrin compound in which Z is a protein can be recombinantly produced.

Another embodiment provided herein is a nucleotide sequence encoding the gastrin compound in which the Z is a protein. Further provided is a cell carrying this nucleotide sequence. The cell is a bacterial or a yeast cell. When the cell is a bacterial cell it can be, for example, a cell of a species of an *Escherichia*, a *Bacillus*, or a *Streptomyces*. When the cell is a yeast cell, it can be a cell of a species of a *Saccharomyces*, a *Kluyveromyces*, a *Schizosaccharomyces* or a *Pichia*.

The gastrin compound generally contains a minimal gastrin component which is at least amino acids at positions 29-34 of SEQ ID NO:2 or positions 12-17 of SEQ ID NO:4. These are located at the carboxy terminus of gastrins that occur in circulation, and in various embodiments additional amino acids for example from gastrin can be present.

The polymer component need not be limited to a protein, but may be a synthetic chemical polymer such as a polyethylene glycol (PEG) or a dextran. When the polymer is a protein, in various embodiments it can be a serum protein, for example, a serum albumin, for example, human serum albumin.

Another embodiment of a gastrin compound provided herein has a structure $C—Y_m—X$, wherein C is Cys or Lys, $Y_m$ is an optional spacer region comprising m amino acid residues of a small neutral amino acid, and X is at least six amino acid residues comprising sequences selected from at least positions 12-17 of gastrin-17 (SEQ ID NO: 3 and 4) and at least positions 29-34 of gastrin-34 (SEQ ID NO: 1 and 2). The gastrin compound further is conjugated to a polymer, for example, is conjugated to a polyethylene glycol (PEG) or a dextran. The gastrin compound further is alternatively conjugated to a protein. In certain embodiments, the gastrin compound further includes a bifunctional cross-linking agent wherein a first reactive end of the cross-linking agent is covalently linked to C. A second reactive end of the cross-linking agent is covalently linked to a polymer or protein. The $C—Y_m—X$ can be produced recombinantly or it can be synthesized by peptide synthesis.

Any of the gastrin compounds provided herein are, in certain embodiments, provided in an effective dose. The gastrin compounds provided herein can further include an agent for immune suppression. The gastrin compounds provided herein can further include a hypoglycemic agent. The gastrin compounds provided herein can further include a pharmaceutically acceptable carrier. The gastrin compounds provided herein can further include a growth factor. For example, in certain embodiments the growth factor is a glucagon-like peptide 1 receptor ligand. Alternatively, in certain embodiments the growth factor is an EGF receptor ligand.

Also provided herein are embodiments of the invention which include a method of manufacture of a medicament for treating a subject having diabetes, comprising formulating a gastrin compound according to any of those described herein, and administering the gastrin compound to the subject. In certain embodiments of the method, frequency of administering the gastrin compound is less than frequency of administration of a native gastrin. The method may further include measuring a physiological indicator of islet neogenesis, for example, measuring fasting blood glucose (FBG). The method may include decreasing insulin dependency.

Yet another embodiment of the invention provides a method of making a gastrin compound, the method being associating an amino acid sequence of a gastrin with a carrier composition. Accordingly, prior to associating the gastrin with the carrier, the gastrin is modified to comprise a cysteine substitution or an additional cysteine residue. The cysteine substitution is a replacement of pyroglutamate. The gastrin amino acid sequence comprises at least positions selected from the group of: residues 29-34 of amino acid sequence. SEQ ID NO: 1; residues 29-34 of amino acid sequence SEQ ID NO: 2; residues 12-17 of amino acid sequence SEQ ID NO: 3; and residues 12-17 of amino acid sequence SEQ ID NO: 4. In certain embodiments, the cysteine is at the amino terminus of the gastrin. Alternatively, prior to associating the gastrin with the carrier, the method includes modifying the gastrin to further include a bifunctional cross-linking agent.

Yet another embodiment of the invention provides a method of manufacture of a medicament for treating a diabetes patient, the method comprising formulating a modified gastrin compound capable of covalently reacting with a serum protein, and administering to the patient the modified gastrin. The modified gastrin includes a sequence of a native gastrin capable of binding to the gastrin/CCK receptor and an amino terminal cysteine or lysine. Accordingly, the sequence of the native gastrin is selected from the group of: residues 29-34 of amino acid sequence SEQ ID NO: 1; residues 29-34 of amino acid sequence SEQ ID NO: 2; residues 12-17 of amino acid sequence SEQ ID NO: 3; and residues 12-17 of amino acid sequence SEQ ID NO: 4.

Also provided herein is a method of manufacture of a medicament for maintaining for an extended period of time an increased gastrin serum level compared with the serum level of a peptide having an amino acid sequence of a gastrin, the method comprising formulating a gastrin compound as described above, and administering the gastrin compound.

Also provided herein is a kit comprising at least one effective dose of a gastrin compound as described herein.

BRIEF DESCRIPTIONS OF DRAWINGS

DETAILED DESCRIPTION OF INVENTION

Figure 1:
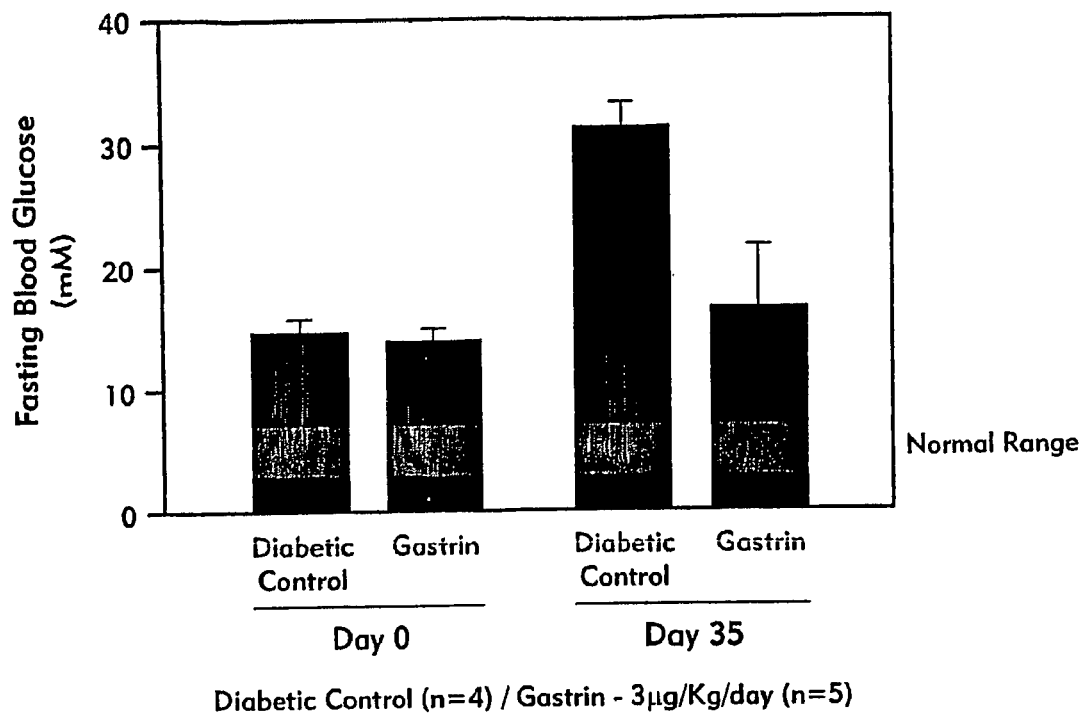
FIG. 1 shows the effect of unmodified gastrin on fasting blood glucose levels of NOD mice with recent onset diabetes after a 14 day treatment.

Use of long acting gastrin compounds can result in decreased clearance of gastrin or reduced degradation of gastrin by enzymes thereby maintaining higher concentrations of plasma gastrin for extended period of time and/or increasing half-life of gastrin thus resulting in increased efficacy. Dosing regimens can be improved by either using lower doses and/or reducing the frequency of administration of gastrin to diabetic patients. In addition, with the conjugation of gastrin to a carrier, it is possible that some of the carriers can also mask gastrin from the immune system, thereby reducing or preventing gastrin provoking immune reaction, as well as increasing the half life and/or maintaining higher concentrations of serum gastrin.

This invention in general embodiments provides compositions having gastrin-like activity herein referred to as gastrin compounds The term "gastrin compounds" as used herein means agents that bind to, interacts with or stimulates the gastrin/CCK receptor. Gastrin compounds include gastrin derivatives and conjugates as well as peptide homologs, that are capable of interacting with the gastrin/CCK receptor. The terms "derivatives" and "conjugates" as used herein are equivalent, and are used to indicate compositions that are chemically related, and can be prepared by synthetic, biological, recombinant or chemical means.

In various embodiments, a "modified" gastrin can be prepared and used to treat a patient having a diabetes. The term, "diabetes" as used herein means any physiologic indication of a shortage of insulin, a production of antibodies against insulin, or an excess of blood sugar or any manifested symptoms of diabetes in any mammal including experimental animal models, and including human forms such as type I and type II diabetes, early stage diabetes, and a pre-diabetic condition characterized by mildly decreased insulin or mildly elevated blood glucose levels. As used herein, the term "mammal" has the usual meaning of any member of Mammalia, and includes humans.

The modified gastrin can be a gastrin derivative or analog comprising a minimal sequence of 6 amino acids (from the C-terminal end), and further having addition of a reactive group such as a cysteine residue capable of undergoing an addition reaction (Refer to SEQ ID 1-4) In various embodiments, the gastrin may extend up to 34 amino acids ("Big" Gastrin or Gastrin-34), wherein at least one reactive amino acid such as a cysteine residue or a lysine residue is added or substituted at the N-terminal end. The addition of the reactive amino acid such as a cysteine can be at a terminal region, and in related embodiments, a spacer region can optionally precede the added reactive amino acid. For example, the spacer can be synthesized biologically as part of, or can be chemically attached to the gastrin amino acid sequence, forming a structure which has a gastrin sequence-spacer-cysteine. For instance, the spacer region can be a sequence of several amino acids such as alanine or glycine. The sequence of amino acids can be alternating amino acids (e.g. glycine/alanine) or can be non-alternating, i.e., can be a random sequence or a particular sequence. The sequence can consist of at least one amino acid.

In alternative embodiments, a bifunctional cross-linking agent which is a reactive component is added to the modified gastrin, particularly to the gastrin having an added reactive group at the amino terminus (e.g., a cysteine), or to a modified gastrin having a spacer, via a homobifunctional or heterobifunctional portion of the crosslinker to generate an a modified gastrin having a reactive group such as a thiol or an amino group at one end. (e.g., to form, as listed from the carboxy terminus, a gastrin-spacer-cys-cross-linker-carrier, a gastrin-cys-cross-linker group-carrier; gastrin-spacer-cys/-cross-linker with reactive group exposed, and a gastrin-cys-cross-linker with reactive group exposed.)

The modified gastrin is then either injected in this state into a patient, or is further conjugated in vitro to one or more plasma components such as whole or fractionated serum obtained from the patient; one or more purified serum protein(s) such as albumin, transferrin or an immunoglobulin; lipids/lipophilic-moieties/hydrophobic moieties; or to polymeric carriers such as dextran or PEG prior to injection. The term polymer as used herein and in the claims includes polymers of amino acids, sugars, nucleosides, synthetic polymers (such as PEG) and mixtures thereof. The polymer can be activated, for instance with a bifunctional crosslinker or via other chemical means prior to conjugation. Administering the activated gastrin compound or the gastrin conjugate results in increased serum half life and/or maintained high plasma concentration of gastrin for an extended period of time, compared with administering native gastrin.

The invention in general embodiments provides gastrin compositions which have a moiety that is a gastrin compound and can be associated with a larger molecule such as a polymer, either non-covalently, or as a covalent conjugate, or as a fusion protein to another peptidic compound having an amino acid sequence. The gastrin compounds provided herein have a longer half-life in circulation in a subject animal or patient, and/or maintain higher concentrations in vivo of the gastrin compounds for an extended period of time compared to the native forms of gastrin. In addition, the invention in other embodiments provides compositions and methods of making and of using the gastrin compounds, provided to the patient either alone or in combination with at least one growth factor, with a hypoglycemic agent, or with an immunosuppressant, for the treatment of diabetes. Examples of growth factors include but are not limited to a EGF receptor ligand such as EGF, a GLP-1 receptor ligand such as GLP-1, prolactin receptor ligand such as prolactin and growth hormone receptor ligand such as growth hormone. Examples of immunosuppressants include but are not limited to cyclosporine, FK506, rapamycin, and daclizumab. Non-limiting examples of hypoglycemic agents include sulfonylureas, meglitinides, biguanides, thiazolidinediones, and alpha-glucosidase inhibitors.

In one embodiment, a gastrin compound can be bound to a comparatively larger structure or a plurality of structures in the blood and still retain the ability to bind target proteins, i.e., a gastrin/CCK receptor. Generally, gastrin, which would be otherwise rapidly degraded in the body, is attached to a carrier protein; using this composition, a longer-term of drug efficacy can be achieved. Alternatively a gastrin compound can be conjugated to a polymeric carrier such as a polyethylene glycol (PEG) or a dextran to achieve similar objectives In certain embodiments, chemical modification of gastrin is used to provide compounds that react covalently or non-covalently to carrier proteins or polymeric carriers, either in vitro (ex vivo) or in vivo. In a related embodiment, the non-covalent interaction is electrostatic or hydrophobic. In related embodiments, conjugation of modified gastrin to the carrier is carried out prior to injection. In other embodiments, the gastrin is modified in such a manner that when injected, will have an enhanced affinity to the carrier in the bloodstream. In another embodiment, long acting gastrin compounds are obtained via chemical modification with no requirement for a carrier protein either in vivo or ex vivo.

In certain embodiments, the carrier protein is a plasma protein. In related embodiment, the plasma protein is an albumin or an immunoglobulin or components of an immunoglobulin. The immunoglobulin or components of the immunoglobulin can be modified or portions deleted prior to conjugation. In certain embodiments, the polymeric carrier is polyethylene glycol or dextran. For instance, activated PEG can be attached to gastrin compound via an amino group in the gastrin compound (Vernonese, F M. Biomaterials 22 (2001)-405-417).

In other embodiments, the gastrin compound which is a sequence of amino acids, is genetically fused with the carrier protein, which is also a sequence of amino acids, prior to injection, using standard recombinant genetic techniques. Gastrin can be fused recombinantly to a carrier protein with or without a linker/spacer, for example, comprising a sequence of small neutral uncharged amino acids. A nucleic acid encoding gastrin can be recombinantly fused or synthesized directly as a fusion to portions or the whole of the carrier protein, and the nucleic acid construct or fusion protein can encode or incorporate a number of additional amino acids to act as a spacer between the two proteins. Recombinant fusion proteins can be expressed in yeast (*Saccharomyces, Pichia*) or in standard bacterial systems, or mammalian or insect cell systems can be used. Following standard procedures for expression and/or purification, the fusion protein can be used therapeutically. Modifications to the sequence of gastrin compound polypeptide can be introduced during construction of the fusion protein if necessary.

In one embodiment, the gastrin compound is modified to introduce a reactive group such as those present on an amino acid such as a lysine or cysteine so that the reactive group upon further contacting another compound such as a carrier protein or carrier non-proteinaceous polymer, can form covalent interactions with the carrier proteins or polymers. For instance, a reactive thiol group can be added to the gastrin molecule through an amino group on lysine, for example, using succinimidyl 3-2-pyridyldithio propionate (SPDP) followed by reduction with DTT to release the active thiol group (("Protein thiolation and reversible protein-protein conjugation. N-Succinimidyl 3-(2-pyridyldithio)propionate, a new heterobifunctional reagent." Carlsson J, Drevin H, Axen R. Biochem J 173, 723-737 (1978)). Further, the bifunctional group can also be added after the cysteine or lysine has been added, so that one reactive end of the crosslinking agent will react with cysteine/lysine while the other reactive end at the other end is left exposed or is conjugated to a carrier.

Thiols can be also incorporated at carboxylic acid groups by EDAC-mediated reaction with cystamine, followed by reduction of the disulfide with DTT. ("Introduction of sulfhydryl groups into proteins at carboxyl sites." Lin C M, Mihal K A, Krueger R J. Biochim Biophys Acta 1038, 382-385 (1990). In a non-limiting example, reaction of an amino group on the lysine residue in gastrin with succinimidyl trans-4-(maleimidylmethyl)cyclohexane-1-carboxylate ("Conjugation of glucose oxidase from *Aspergillus niger* and rabbit antibodies using N-hydroxysuccinimide ester of N-(4-carboxycyclohexylmethyl)-maleimide." Yoshitake S, Yamada Y, Ishikawa E, Masseyeff R. Eur J Biochem 101, 395-399 (1979)) introduces a thiol reactive group at amino sites of gastrin that can subsequently react with cysteine residues of the carrier protein or free thiol group on the activated polymer.

A gastrin compound-carrier complex can include additional modular components including a spacer arm or element or other component that can facilitate preparation or isolation of the gastrin compound-carrier complex or enhance or maintain the functional activity of the gastrin compound. The spacer arm can be one or more amino acids, peptide, a peptidomimetic, or a small organic molecule, and can comprise homobifunctional or heterobifunctional crosslinking agents or chitin oligomers or polyethyelene glycol or related polymers.

In another embodiment, the carrier and gastrin compound can be covalently crosslinked with or without a spacer arm. Examples of non-spacer arms (zero-length crosslinkers) include EDC. Homobifunctional crosslinkers that generate a spacer arm can be for instance disuccinimidyl suberate and heterobifunctional crosslinkers that generate a spacer arm can be for instance 2-iminothiolane, succinimidyl 6-[3-(2-pyridyldithio)propionamido]hexanoate (LC-SPDP) and 4-(N-maleimido methyl)cyclohexane-1-carboxylate (SMCC).

In various embodiments, the gastrin compound is associated with a larger carrier moiety such as a polymer, for example a protein. As the association may be covalent or non-covalent, the protein may be considered to be a carrier protein. Classes of carrier proteins can possess the properties of being non-antigenic, i.e., are native human proteins, and are being capable of sustained maintenance in circulation. An ideal carrier protein is one normally found in the human circulatory system.

As used herein, the term "gastrin/CCK receptor ligand" encompasses any compound that binds to, interacts with or stimulates the gastrin/CCK receptor. Examples of such gastrin/CCK receptor ligands are given in U.S. Pat. No. 6,280,301 issued Sep. 11, 2001, and include various forms of gastrin, such as gastrin 34 (big gastrin), gastrin 17 (little gastrin or small gastrin), gastrin 14, gastrin 13, gastrin-10, and gastrin 8, pentagastrin, tetragastrin; various forms of cholecystokinin such as CCK 58, CCK-33, CCK 22, CCK 12 and CCK 8; and other gastrin/CCK receptor ligands. In general, gastrin/CCK receptor ligands share a carboxy terminal amino acid sequence Trp-Met-Asp-Phe-amide. The aforementioned methionine (Met) can be replaced by a leucine. Also contemplated are active analogs, fragments and other modifications of the above, including both peptide and non-peptide agonists or partial agonists of the gastrin/CCK receptor such as A71378 (Lin et al., Am. J. Physiol. 258 (4 Pt 1): G648, 1990).

Small forms of gastrin such as gastrin 17 are economically prepared by peptide synthesis, and synthetic peptides are commercially available. Synthetic human gastrin 17 such as human gastrin 17 having methionine or leucine at position 15 are also available from Bachem A G, Bubendorf, Switzerland, and from Researchplus. Gastrin peptides as found in nature are carboxyl-terminally amidated peptides, and amidation of the carboxyl terminus amino acid is within the scope of gastrin compounds herein.

Gastrin/CCK receptor ligands include also active analogs, fragments and other modifications of the above ligands, which for example share amino acid sequence with an endogenous mammalian gastrin, for example, share 60% sequence identity, or 70% identity, or 80% identity. Such ligands also include compounds that increase the secretion of endogenous gastrins, cholecystokinins or similarly active peptides from sites of tissue storage. Examples of these are the gastric releasing peptide, omeprazole which inhibits gastric acid secretion, and soya bean trypsin inhibitor which increases CCK stimulation The sequence of big gastrin-34 and small gastrin-17 are shown herein. Big gastrin-34 is essentially an extension form of small gastrin-17 having an additional amino acid sequence at the N-terminal end. Big gastrin is cleaved in vivo to release gastrin-17. The symbol "Glp" at the N-terminal end is a pyroglutamate residue, which is a naturally cyclized form of glutamate. In various embodiments, gastrins having an N-terminal pyroglutamate residues are modified to contain N-terminal cysteine or lysine residues by either replacing the pyroglutamate with a glutamate or glutamine, or deleting the pyroglutamate. Further, each of a gastrin 34 and gastrin-17 can be used in a modified form that has a methionine or a leucine at position 32 as shown herein in SEQ ID No: 1-2, respectively, or at position 15 as shown in SEQ ID No: 3-4, respectively.

(SEQ ID NO: 1)
N-terminal Glp-Leu-Gly-Pro-Gln-Gly-Pro-Pro-His-Leu-Val-Ala-Asp-Pro-Ser-Lys-Lys-Gln-Gly-Pro-Trp-Leu-Glu-Glu-Glu-Glu-Glu-Ala-Tyr-Gly-Trp-Met-Asp-Phe- NH$_2$.

(SEQ ID NO: 2)
N-terminal Glp-Leu-Gly-Pro-Gln-Gly-Pro-Pro-His-Leu-Val-Ala-Asp-Pro-Ser-Lys-Lys-Gln-Gly-Pro-Trp-Leu-Glu-Glu-Glu-Glu-Glu-Ala-Tyr-Gly-Trp-Leu-Asp-Phe- NH$_2$.

(SEQ ID NO: 3)
N-terminal Glp-Gly-Pro-Trp-Leu-Glu-Glu-Glu-Glu-Glu-Ala-Tyr-Gly-Trp-Met-ASp-Phe- NH$_2$.

(SEQ ID NO: 4)
N-terminal Glp-Gly-Pro-Trp-Leu-Glu-Glu-Glu-Glu-Glu-Ala-Tyr-Gly-Trp-Leu-Asp-Phe- NH$_2$.

In certain embodiments, the gastrin compound which is a fusion, for example, of a gastrin amino acid sequence with an optional spacer of amino acids at the amino terminus of the gastrin sequence, and having a protein carrier, can be provided transgenically to a subject In an embodiment of a nucleic acid construct for transgenic expression of such a fusion protein, a human preprogastrin peptide precursor gene is fused to a gene encoding a carrier protein, with or without a spacer, by techniques similar to those as shown in U.S. Pat. No. 5,885,956.

The method for treating diabetes mellitus in an individual in need thereof includes administering to the individual a composition that provides a gastrin compound and a FACGINT such as EGF, GLP-1, prolactin and growth hormone. Included are derivatives, analogs, and conjugates of these FACGINT. As used herein, the term "FACGINT" means a factor that complements gastrin for islet neogenesis therapy. The phrase, "a FACGINT" as used herein can also mean "one or more FACGINTs" or "at least one FACGINT".

The term "FACGINT" includes a large variety of growth factors and growth hormones, agents that modify one or more of the factors hormones, and ligands and effectors for one or more receptors involved in binding of these growth hormones and growth factors as these terms are generally understood, exemplified but not limited to: EGF receptor ligand, a PTH-related protein (PTHrP) receptor ligand such as PTHrP (PTHrP; Garcia-Ocana, A. et. al., 2001, J. clin. Endocrin. Metab. 86: 984-988); a hepatocyte growth factor (HGF) receptor ligand such as HGF (HGF; Nielsen, J. et al., 1999, J Mol Med 77: 62-66); a fibroblast growth factor (FGF) such as FGF, a keratinocyte growth factor (KGF) receptor ligand such as KGF; a nerve growth factor (NGF) receptor ligand such as NGF; a gastric inhibitory polypeptide (GIP) receptor such as GIP; a transforming growth factor beta (TGFβ) receptor ligand such as TGFβ (U.S. patent application 2002/0072115 published Jun. 13, 2002), a laminin receptor ligand such as laminin-1; an islet neogenesis associated protein (INGAP) receptor ligand such as INGAP; a bone morphogenetic factor (BMP) receptor ligand such as BMP-2; a vasoactive intestinal peptide (VIP) receptor ligand such as VIP; a glucagon-like peptide 1 receptor ligand such as GLP-1 and exendin-4, glucagon-like peptide 2 (GLP-2) receptor ligand such as GLP-2, and dipeptidyl peptidase IV inhibitors which indirectly affect the levels of GLP-1 (Hughes, T. et al., 2002, Am Diabetes Assoc Abstract 272-or) by inhibiting an enzyme involved in its integrity, a REG receptor ligand such as REG protein; a Growth hormone (GH) receptor ligand such a GH, a Prolactin (PRL) receptor ligand such as PRL and placental lactogen (PL); an Insulin-like growth factor (Type 1 and 2) receptor ligands such as IGF1 and IGF-2; an Erythropoietin (EPO) receptor ligand such as EPO (http://www.drinet.org/html/august_2002_.htm); a betacellulin (also considered to be a member of the EGF family); an Activin-A receptor ligand such as Activin-A; a vascular endothelial growth factor (VEGF) receptor ligand such as VEGF; a bone morphogenesis factor (BMP) receptor ligand such as BMP-2; a vasoactive intestinal peptide (VIP) receptor ligand such as VIP; a vascular endothelial growth factor (VEGF) receptor ligand such as VEGF; a pituitary adenylate cyclase activating polypeptide (PACAP) receptor ligand such as PACAP; a granulocyte colony stimulating factor (G-CSF) receptor ligand such as G-CSF; a granulocyte-macrophage colony stimulating factor (GM-CSF) receptor ligand such as GM-CSH; a platelet-derived growth factor (PDGF) receptor ligand such as PDGF; and a Secretin receptor ligand such as secretin.

For any of the growth factors, enzymes, enzyme inhibitors, peptide, protein and hormone compounds herein that are indicated to be an exemplary FACGINT, all known analogues and derivatives, whether naturally occurring or made by mutagenesis or designed and synthesized shall be considered equivalent to that FACGINT. Also considered among equivalents are conjugates, i.e., compositions derived by addition of one or more of a chemical group, and mixtures thereof. Encoding genes may be altered by, for example, oligonucleotide directed mutagenesis to produce FACGINT analogues thereof, such as the human recombinant analogues. Further, an identity or location of one or more than one amino acid residue may be changed by targeted mutagenesis. The primary amino acid sequence of the protein may be augmented by conjugates, as by glycosylation, acylation, or by addition of any other supplementary molecules, such as one or more of a lipid, a phosphate, a sulphate and/or an acetyl group. Further, individual amino acid residues in the chain may be modified by oxidation, reduction, or other derivatization. The FACGINT may be cleaved to obtain any fragments which retain activity. A prodrug or a metabolite of a FACGINT is equivalent to that FACRUG. The whole polypeptide or protein or any fragment can be fused with any other peptide or protein such as immunoglobulins and other cytokines. Conjugates may include, for example, a composition comprising the FACGINT coupled to a non-naturally occurring polymer comprising a polyethylene glycol moiety. The term also encompasses derivatives obtained by chemically modifying one or more amino acid residues of the parent peptide, for instance by alkylation, acylation, ester formation or amide formation. Alternatively, agents that induce synthesis of the FACGINT or mimic the action of the FACGINT are contemplated as equivalent compounds. The singular form, "FACGINT", may mean any one or more compounds from the exemplary FACGINTs shown herein. The terms "derivatives" and "conjugates" as used herein are equivalent, and are used to indicate compositions that are chemically related, and can be prepared by synthetic, biological, or recombinant or chemical means.

The term, "receptor ligand" as used herein in connection with a receptor for a particular ligand shall mean any compositions that binds to, interacts with, or stimulates that receptor.

A receptor ligand includes within the scope of the definition a receptor agonist, for the receptor for any particular FACGINT, whether or not the agonist is structurally related to the FACGINT.

The term, "prolactin" as used herein means any polypeptide which shares substantial sequence similarity with an endogenous mammalian prolactin as this term is known in the art of protein factors, for example, human prolactin, and which possesses the activity of a prolactin. Endogenous human prolactin is a 199 amino acid polypeptide produced by the pituitary gland. The term encompasses prolactin analogs which are deletions, insertions, or substitution mutants of endogenous prolactin, and retain the activity, and includes prolactins from other species and naturally occurring variants. The prolactin function includes a composition having agonist activity for the prolactin receptor, as disclosed in U.S. Pat. No. 6,333,031 (activating amino acid sequence) and U.S. Pat. No. 6,413,952 (metal complexed receptor ligand agonist), and G120RhGH, which is an analog of human growth hormone that acts as a prolactin agonist (Mode et al., 1966, Endocrinol. 137(2): 447-454), and a ligand for the prolactin receptor as described in U.S. Pat. Nos. 5,506,107 and 5,837,460.

PRL, GH and PL are members of a family of polypeptide hormones that share a structural, immunological and biological functions (reviewed in, "Pancreatic Growth and Regeneration", Ed. N. Sarvetnick, Ch. 1. Brejie, T. et al., 1997), and therefore referred to herein as the PRL/GH/PL family. PRL and GH are secreted by the anterior pituitary of vertebrate animals. PRL is involved in a broad range of biological functions that include osmoregulation, reproduction, lactation, and immunomodulation. GH is associated with physiological processes related to growth and morphogenesis. The related receptor ligands are referred to as "PRL/GH/PL" receptor ligands. The FACGINTs can be classified into various groups based on structural similarity of the peptides and proteins, functional similarity with respect to complementation of gastrin, functional similarity with respect to binding of one or more receptors, and these groups are each within the scope of various embodiments of the invention.

Glucagon-like peptide-1 is synthesized in intestinal endocrine cells in molecular forms GLP-1 (having residues conventionally designated as positions 7-36) which is an amide, and similarly as GLP-1 (7-37). Initial studies of GLP-1 biological activity in utilized the full length N-terminal extended forms of GLP-1 (1-37 and 1-36 which latter is an amide). The larger GLP-1 molecules were generally lacking biological activity. It was later found that removal of the first six amino acids resulted in a shorter version of the GLP-1 molecule having substantially enhanced biological activity.

The majority of circulating biologically active GLP-1 is found in the GLP-1 (7-36)amide form, with lesser amounts of the bioactive GLP-1 (7-37) form also detectable. See Orskov, C. et al., Diabetes 1994, 43: 335-339. Both peptides show about the same amount of biological function. GLP-1 is secreted from gut endocrine cells in response to nutrient ingestion and plays multiple roles in metabolic homeostasis following nutrient absorption. Regulation of GLP-1 occurs by N-terminal degradation of the peptide by Dipeptidyl Peptidase (DPP-IV)-mediated cleavage at the position 2 alanine residue. For an overview, see DPP-IV. The biological activities of GLP-1 include stimulation of glucose-dependent insulin secretion and insulin biosynthesis, inhibition of glucagon secretion and gastric emptying, and inhibition of food intake. GLP-1 appears to have a number of additional effects in the GI tract and central nervous system, as reviewed in Drucker, D., Endocrin 142: 521-527, 2001. Exemplary GLP-1 compositions include: BIM 51077 (GLP-1 analog resistant to DPP-IV digestion, available from Beaufour Ipsen); AC2592 (GLP-1, from Amylin, San Diego go CA); ThGLP-1 (GLP-1, modified amino acids and fatty acid attachment, from Theratechnologies, Saint-Laurent, Quebec, Canada); DAC: GLP-1 (Conjuchem, Montreal, Quebec, Canada); CJC-1131 or DAC™:GLP-1 (GLP-1 analog engineered for covalent coupling to albumin, Conjuchem), LY315902 and sustained release LY315902 (DDP-IV resistant GLP-1 analog from Eli Lilly, Indianapolis, Ind.); low molecular weight GLP-1 mimetic, Albugon (albumin: GLP-1 fusion peptide from Human Genome Sciences, Rockville, Md.); Liraglutide or NN2211 (long acting GLP-1 derivative that is obtained by acylation of the GLP-1 molecule, which upon entering the bloodstream, is extensively bound to albumin which protects it from degradation by DPPIV and reduces renal clearance; Elbrond et al., Diabetes Care 2002 Aug. 25(8): 1398-404).

Exendin-4 is a novel peptide from *Heloderma suspectum* (Gila monster) venom, having 53% homology with GLP-1 (7-36)amide. It functions as a long-acting potent agonist of the glucagon-like peptide 1 (GLP-1) receptor, as it is resistant to degradation by DDP-IV. Exendin-4 has properties similar to GLP-1, and regulates gastric emptying, insulin secretion, food intake, and slucagon secretion. Examples of exendin-4 include exenatide (synthetic form also known as AC2993, Amylin); exenatiate LAR (long acting form); ZP10 (modified exendin-4 having addition of six lysine residues, Aventis/Zealand Pharma); and AP10 (long acting formulation, Alkermes, Cambridge Mass.). Physiological studies indicate that sustained expression of exendin-4 in transgenic mammals does not perturb glucose homeostasis, cell mass or food intake (Biaggio, L. et al. J Biol Chem 275: 34472-34477, 2000), so that the physiological effects of exendin-4 are not completely understood.

Dipeptidyl peptidase IV (DPP-IV) inhibitors refer to compounds that inhibit activity of DPP-IV, a membrane-associated peptidase of 766 amino acids that includes in its substrates GLP-1, GLP-2 and GIP. DPP-IV-mediated inactivation of GLP-1 is a determinant of GLP-1 bioactivity in vivo. Examples of DPP-IV inhibitors include isoleucine thiazolidide, valine-purrolidide, NVP-DPP738 (Novartis, Cambridge, Mass.), LAF237 (Novartis), P32/98 (Probiodrug AG, Halle, Germany), and P93/01 (Probiodrug).

As used herein, the term "EGF receptor ligand" encompasses compounds that stimulate the EGF receptor such that when gastrin/CCK receptors in the same or adjacent tissue or in the same individual are also stimulated, neogenesis of insulin-producing pancreatic islet cells is induced. Examples of such EGF receptor ligands include full length EGF, which is EGF1-53, and further include EGF1-48, EGF1-49, EGF1-52, and fragments and active analogs thereof. Other examples of EGF receptor ligands are TGFα forms that include 1-48, 1-47, 1-51, and amphiregulin and pox virus growth factor as well as any EGF receptor ligands that demonstrate the same synergistic activity with gastrin/CCK receptor ligands. These include active analogs, fragments and modifications of the above. See also, Carpenter and Wahl, Chapter 4, in Peptide Growth Factors (Eds. Sporn and Roberts), Springer Verlag, 1990.

The group of compounds that comprises the EGF receptor ligands further includes "modified EGF", which includes variants of normal or wild type EGF. Modifications have been shown to affect one or more biological activity such as the rate of clearance of EGF. The term includes peptides having an amino acid sequence substantially similar to that of human EGF, for example, with one or a few amino acid substitutions at various residue positions.

Recombinant EGF forms have been genetically engineered to have alterations in structure and activities, for example, EGF having a methionine at position 21 replaced by a leucine residue has been described (U.S. Pat. No. 4,760,023). Recombinant human EGF (hEGF) having 51 residues, i.e., lacking the two C-terminal residues at positions 52 and 53 of hEGF, and having a neutral amino acid substitution at position 51, retain EGF activity and are more resistant to protease degradation during a microbial production process, and following administration to a subject. A series of nucleic acid molecules have been described that encode a family of proteins that have significant similarity to EGF and, TGFα (WO 00/29438). EGF muteins (mutated EGF) having histidine at residue 16 replaced with a neutral or acidic amino acid have been described (WO 93/03757), such forms retaining activity at low values of pH. Chemical analogues and fragments of EGF and TGFα retain ability to bind various members of the EGF receptor family (U.S. Pat. No. 4,686,283). Various modifications of EGF or TGFα confer advantageous properties affecting one or more of recombinant protein production, in vitro and in vivo stability, and in vivo activity. A exemplary recombinant modified EGF receptor ligand used in the Examples herein is a C-terminus deleted form of human EGF of 51 amino acids in length, having asparagine at position 51 (referred to herein as EGF51N), which retains substantially full I.N.T.™ activity, and has in vivo and/or in vitro stability that is that is at least about as great or greater than normal or wild type hEGF (S. Magil et al., published May 15, 2003 as PCT/US02/33907, and incorporated by reference herein in its entirety).

The term, "growth hormone" as used herein encompasses any polypeptide that shares substantial amino acid sequence identity with an endogenous mammalian growth hormone and possesses a biological activity of a mammalian growth hormone. Human growth hormone is a polypeptide containing 191 amino acids in a single chain, and a molecular weight of about 22 kDal (Goeddel et al., 1979, Nature 281: 544-548; Gray et al., 1985, Gene 39: 247-254). The term encompasses analogs having deletions, insertions or substitutions and growth hormones from other species and naturally occurring variants. See Cunningham et al., 1989, Science 243: 1330-1336, and 1989, Science 244: 1081-1085; and WO 90/05185, and U.S. Pat. No. 5,506,107.

The term "treating" or "ameliorating" as used herein means reducing or eliminating one or more symptoms of diabetes. The term, "diabetes" as used herein means any physiologic indication of a shortage of insulin, a production of antibodies against insulin, or an excess of blood sugar or any manifested symptoms of diabetes in any mammal including experimental animal models, and including human forms such as type I and type II diabetes, early stage diabetes, and a pre-diabetic condition characterized by mildly decreased insulin or mildly elevated blood glucose levels. A "pre-diabetic condition" describes a mammal suspected of having a diabetic or related condition, for example, not formally diagnosed with diabetes, but demonstrating a symptom in terms of insulin or glucose level, and susceptibility to diabetes or a related condition due to family history, genetic predisposition, or obesity in the case of type II diabetes, or has previously had diabetes or a related condition and is subject to risk of recurrence.

As used herein, the term "immunosuppressant" or "agent for immune suppression" means any agent that suppresses immune response. Exemplary immunosuppressant agents are shown in Table 1, and any derivatives of those agents or functional equivalents are considered appropriate for embodiments of the invention as described herein and in the claims. Immunosuppressive agents, in Table 1 or other equivalent agents are administered as supplied by the manufacturers, normalizing to body weight of the subject as is known by one of skill in the pharmacological arts. For example, Tacrolimus is generally administered by injection or orally, and Sirolimus is generally administered orally

TABLE 1

Exemplary agents for immune suppression, and commercial sources

| Names | Company | Nature |
|---|---|---|
| 2-amino-1,3-propanediol derivatives | Novartis | Used for preventing or treating chronic rejection in a patient receiving an organ or tissue allo-or xeno-transplant |
| 2-amino-2[2-(4-octylphenyl)ethyl]propane-1,3-diol hydrochloride | Yoshitomi Pharmaceutical Industries, Ltd | Immunosuppression, from accelerated lymphocyte homing |
| 40-O-(2-hydroxyethyl)-rapamycin, SDZ-RAD, Everolimus (Certican ®) | Novartis Pharmaceuticals | Sirolimus (rapamycin) derivative, used for acute kidney rejection; reduces rejection and graft vasculopathy following heart transplantation by inhibiting cell proliferation |
| 6-(3-dimethyl-aminopropionyl) forskolin | Matsumori Akia Nippon Kayaju Co Ltd | Immunosuppressing action useful also for treating autoimmune disease |
| 6-mercaptopurine (Purinethol ®, 6-MP) | Glaxo SmithKline | Used to treat Crohn's disease, inflammatory bowel disease and for organ transplant therapy |
| ABX-CBL (CBL-1) | Abgenix | Mouse monoclonal AB targeted against human T-cell, B cells, NK cells and monocytes, fortreatment of steroid-resistant graft vs host diseases, potential use in treatment of inflammatory and autoimmune disorders |
| Alefacept (human LFA-3 IgG1 fusion protein, AMEVIVE ®) | University of Utah-Dermatology Dept/BIOGEN | Knocks out causative memory T-lymphocytes; Used to treat psoriasis, a T-cell mediated inflammatory disorder |
| HLA-B2702 peptide (Allotrap ®) | SangStat Medical | Human peptide, blocks action of NK cells and T-cell mediated toxicities, used for prevention of first kidney allograft rejection |
| Antisense ICAM-1 inhibitor (ISIS 2302), Enlimomab, BIRR1, Alicaforsen) | ISIS-Boehringer Ingleheim | Mouse monoclonal AB blocks white blood cell adhesion to T-cell surface molecule (ICAM-1r); treatment of kidney transplant rejection |
| Azathioprine (Imuran ®, Azasan ®) | Generic, Glaxo SmithKline, Prometheus Laboratories, aaiPharma | Treatment of rheumatoid arthritis and prevention of kidney transplant rejection, and other autoimmune or inflammatory disorders such as inflammatory bowel disease |
| BTI-322 | MedImmune | Mouse derived monoclonal AB targeted to CD2 receptor; used for prevention of first-time kidney rejection, and treatment of resistant rejection |
| Cladribine (Leustatin ®) | Boehringer Ingleheim | Antimetabolite and immunosuppressive agent that is relatively selective for lymphocytes; used to treat lymphoid malignancies, e.g., hairy-cell leukemia. |

TABLE 1-continued

Exemplary agents for immune suppression, and commercial sources

| Names | Company | Nature |
| --- | --- | --- |
| Cyclophosphamide (CTX, Neosar ®, Cytoxan ®, Procytox ®) | Generic | Immunosuppressant t for treatment of arthritis and other auto-immune disorders and cancers |
| Cyclosporine (cyclosporin A, cyclosporin) (Sandimmune ®, Neoral ®, SangCya ®) | Novartis | 11 amino acid cyclic peptide; blocks helper T-cell, immunosuppressant used in organ transplant therapy and other immune diseases |
| Demethimmunomycin" (L-683,742: also described as 31-desmethoxy-31-hydroxy-L-683,590) | Merck & Co | Treatment of autoimmune diseases, infectious diseases and/or prevention of organ transplant rejections |
| Dexamethasone (Decadron, Dexone, Dexasone) | Generic | An adrenocorticoid, effective immunosuppressant in various disorders |
| Docosahexaenoic acid (DHA) | Not applicable | Immunosuppressant by that lowers the proportion of T cells expressing CD4 or CD8, blocks antigen recognition process; Taku et al., Journal of Agricultural and Food Chemistry, 2000; 48(4): 1047 |
| FTY720 (oral myriocin derivative) | Novartis Pharmaceuticals | Alters lymphocyte infiltration into grafted tissues; used for prevention of organ rejection in kidney transplants |
| Glatiramer acetate (co-polymer-1, Copaxone ®) | Teva Pharmaceuticals | Synthetic peptide copolymer; decoy that mimics structure of myelin so immune cells bind Copaxone instead of myelin; for multiple sclerosis |
| Glial fibrillary acidic protein (GFAP) | CalBiochem; Synx Pharma | Possesses immunosuppressive activities in diabetic animal models; Winer et al., Nature Medicine 9: 198 (2003) |
| Gusperimus, (15-deoxyspergualin (Spanidin ®) | Bristol Myers-Squibb | Intravenous immunosuppressant; suppresses production of cytotoxic T-cells, neutrophils and macrophages |
| hu1124 (anti-CD11a) | XOMA | Humanized monoclonal antibody; targets CD11a receptor on surface of T cells to selectively inhibit immune system rejection of transplanted organs |
| Infliximab (Remicade ®) | Centocor (affiliate of Johnson and Johnson) | Monoclonal AB, binds and inactivates human TNF-alpha and; used to treat Crohn's disease and rheumatoid arthritis |
| Interferon | Various companies including Serono, Biogen etc | Immunomodulatory properties |
| ISAtx247 | Isotechnika | Used to treat autoimmune diseases such as rheumatoid arthritis and psoriasis |
| isotretinoin | | Immunosuppressant, reduces ability of T cells to proliferate in response to immune challenge. Vergelli et al., Immunopharmacology, 1997, 31: 191. |

TABLE 1-continued

Exemplary agents for immune suppression, and commercial sources

| Names | Company | Nature |
|---|---|---|
| Medi-500 (T10B9) | MedImmune | Intravenous monoclonal AB that targets human T-cells; treats acute kidney rejection and graft-vs-host disease |
| Medi-507 | MedImmune/Bio-Transplant | Intravenous humanized AB directed against CD2 T-cell; used to treat corticosteroid-resistant graft vs host disease and prevention of kidney rejection |
| Methotrexate (Rheumatrex ®, Amethopterin, Trexall ®) | Wyeth Lederle, Generic | Antimetabolite used to treat Crohn's disease, severe psoriasis, and adult rheumatoid arthritis (and as an anti-cancer drug) |
| Mitoxantrone (Novantrone ®) | Immunex | Antiproliferative effect on cellular immune system including T-cells, B-cells and macrophages; used to treat hormone-refractory prostate cancer, acute myelogenous leukemia and multiple sclerosis |
| mycophenolate mofetil (CellCept ®) | Roche | Proliferation of T and B lymphocytes by blocking the synthesis of purine nucleotides; used in organ transplant therapy and inflammatory bowel disease |
| OKT4A | R. W. Johnson Pharmaceutical Research Institute | Mouse monoclonal AB targeted against human CD4 T cell; used for prevention of kidney transplant rejection when used in combination with other immunosuppressant drugs |
| Muromonab-CD3 (Orthoclone OKT3 ®)( ) | R. W. Johnson Pharmaceutical Research Institute | Monoclonal AB that binds to receptor sites on T-cells, preventing activation by transplanted tissue |
| Prednisolone (Deltasone ®, Oraone ®) | | Corticosteroid, suppresses inflammation associated with transplant rejection |
| basiliximab (Simulect ®) | Novartis Pharmaceuticals | Monoclonal AB that binds to receptor sites on T-cells, preventing activation by transplanted tissue (renal transplant) |
| S100β | glial protein | Possesses immunosuppressive activities in diabetic animal models |
| Sirolimus, Rapamycin (Rapamune ®) | Wyeth-Ayerst Laboratories | Immunosuppressant and potent inhibitor of cytokine (e.g.IL-2)-dependent T-cell proliferation (kidney transplant) |
| Tacrolimus (Prograf; FK-506) | Fujisawa | Interferes with IL-2 TCR communication |
| Antithymocyte immunoglobulin (ATGAM, Thymoglobulin ®) | SangStat Medical Corporation, Pharmacia and Upjohn | Anti-human thymocyte immunoglobulin; used in reversal of acute kidney transplant rejection and will likely be used off-label for transplant induction therapy |
| efalizumab (Xanelim ®) | XOMA | T-cell modulator that target T-cells through interactions with adhesion molecules on endothelial cell surface, target migration of T-cells into the skin and target activation of T-cells; Used to treat Psoriasis |

TABLE 1-continued

Exemplary agents for immune suppression, and commercial sources

| Names | Company | Nature |
|---|---|---|
| Daclizumab (Zenapax ®), HAT (Humanized Anti-Tac), SMART anti-Tac, anti-CD25, and humanized anti-IL2-receptor | Protein Design Laboratories/Roche | Monoclonal AB inhibits binding of IL-2 to IL-2 receptor by binding to IL-2 receptor; suppresses T cell activity against allografts (renal transplant) |

Hypoglycemic agents or drugs can be insulin response enhancers, and are typically used as for glycemic control in diabetic patients. These agents include but are not limited to sulfonylureas (e.g. acetohexamide, chlorpropamide, tolazamide, tolbutamide, glyburide, glipizide, glimepiride), meglitinides (e.g. repaglinide, nateglinide), biguanides (e.g. metformin), thiazolidinediones (e.g. pioglitazone, rosiglitazone), alpha-glucosidase inhibitors (e.g. Miglitol), glucagons antagonists, potassium channel openers, insulin sensitizers, hepatic enzyme inhibitors, glucose uptake modulators, compounds modifying lipid metabolism and compounds lowering food intake. Combinations of these agents can be used with the gastrin compounds provided herein.

As used herein the term mammal shall include without limitation any members of the Mammalia, such as a human, an ape, a rodent such as a mouse or rat, a dog, a cat, an agriculturally important animal or a protein pig, a goat, a sheep, a horse, or an ape such as a gorilla or a chimpanzee. An individual mammal may be non-diabetic, pre-diabetic, or diabetic, as specified herein.

Modes of systemic administration include, but are not limited to, transdermal, intrathecal, intramuscular, intraperitoneal, intravenous, subcutaneous, intranasal, and oral routes. The compounds may be administered by any convenient route, for example, by infusion or bolus injection, by absorption through epithelial or mucocutaneous linings (e.g., oral mucosa, rectal, vaginal, nasal, and intestinal mucosa, etc.), and may be administered together with other biologically active agents. An exemplary route of administration is systemic, for example, by subcutaneous injection. The gastrin compound if administered with a FACGINT or immunosuppressant or a hypoglycemic agent can be administered in a single combined dose, or the components can be administered separately in any order.

Methods of Preparation of Compositions
  Synthesis of Gastrin Peptides
  Gastrin peptides can be produced by any suitable means, such as expression in a recombinant host cell or by chemical synthesis. For the latter, gastrin peptides for instance can be synthesized by using solid phase Fmoc peptide synthesis on a polydimethylacrylamide gel resin. The polypeptide is then purified by standard methods.
  Conjugating Partners/Carriers
  Conjugating partners/carriers include plasma components such as serum obtained from the patient, purified serum protein(s) such as albumin, transferrin or an immunoglobulin, red blood cell proteins such as glycophorin A and AE-1, sugar binding proteins such as lectin, inactivated enzymes, phosphate and sulfate binding proteins, cholic acid, lipids binding proteins, lipids/lipophilic moieties/hydrophobic moieties; polymeric carriers such as dextran or polyethylene glycol. When gastrin is conjugated to the lipids/lipophilic moieties, it is possible that these conjugates once injected can interact either non-covalently or covalently with serum proteins such albumin which is known to bind to fatty acids, for instance or lipid binding proteins in the serum. For the purposes of the compositions and methods herein, serum and plasma may be used interchangeably. In order to conjugate gastrin to a carrier, the carrier may first need to be activated via the introduction of a reactive group. In some cases, the carrier can already contain at least one reactive group, for instance cysteine 34 on albumin. After activation of the carrier (if necessary), the carrier is conjugated to gastrin compound. In general, carriers can be covalently attached to proteins via reactive groups in the protein chain, such as thiol groups, alpha and epsilon amino groups, carboxyl groups or aromatic rings, all of which may already be present, or can be added by preliminary chemical modification of the protein which can be either incorporated during chemical synthesis or by chemically modifying existing gastrin peptides or by modifying a protein's amino acid sequence, using known molecular biology methods. For instance, carrier can be attached to the protein's epsilon amino groups in lysine residues or the thiol groups on cysteine residues located at the N-terminal end. Alternatively, the carrier can be attached to the protein via a heterobifunctional or homobifunctional crosslinking agent.

Plasma Proteins
  Plasma protein binding can be an effective means of improving the pharmacokinetic properties of otherwise short-lived molecules such as gastrin. One aspect of plasma proteins is a native molecular mass larger than the kidney filtration cutoff (~45 kDa), and thus an extended residence time in plasma. Plasma proteins include but are not limited to Albumin, Alpha-1 Acid Glycoprotein, Alpha-1-Antichymotrypsin, Alpha-1-Antitrypsin, Alpha-2-Antiplasmin, Alpha-2-HS-Glycoprotein, Alpha-2-Macroglobulin, Angiotensinogen, Antithrombin III, Apolipoprotein AI (HDL), Apolipoprotein AII (HDL), Apolipoprotein B (LDL), Apolipoprotein CI (VLDL), Apolipoprotein CII (VLDL), Apolipoprotein CIII (VLDL), Apolipoprotein E (VLDL), Apotransferrin, C1 Esterase Inhibitor, Ceruloplasmin, Ferritin, Fibrinogen, GC Globulin, Haptoglobin (mixed type), Hemoglobin, Immunoglobin A, Immunoglobin A1, Immunoglobin A1, Immunoglobin A2, Immunoglobin D, Immunoglobin E, Immunoglobin G, Fab Fragment, Immunoglobin G, Fc Fragment, Immunoglobin G, Immunoglobin G1, Immunoglobin G2, Immunoglobin G3, Immunoglobin G4, Immunoglobin M, μ Chain, Immunoglobin M, Fc$_5$μ, Immunoglobin M, Immunoglobulin heavy chain (H) Immunoglobulin light chain (L)-K-light chains, gamma-light chains, Fab fragment of an immunoglobulin Fc fragment of an immunoglobulin, Lactoferrin, Lipoprotein a, [Lp(a)], Lipoprotein (high density), Lipoprotein (Low Density), Lipoprotein (Very Low Density), Prealbumin, Prothrombin, Prothymosin-α, Rheumatoid Factor, Steroid binding proteins, Transcortin, Thyroxine-binding globulin. Transferrin and α-fetoprotein. A list of plasma proteins can be found in Anderson and Anderson, Molecular and Cellular Proteomics 2002, 1.11: 845.

Human serum albumin has a molecular mass of ~67 kDa, a half-life of 19 days in circulation, and is the most abundant protein in plasma human. Albumin consists of 585 amino acids forming a single polypeptide chain. Albumin interacts with a large number of compounds including physiological ligands such as long chain fatty acids, certain therapeutic drugs such as Warfarin and Valproate and inorganic ligands such as calcium.

The antibody/immunoglobulin can include a complete immunoglobulin or fragment thereof, where immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, fragments, aggregates, polymers, or conjugates of immunoglobulins can be used where appropriate. The antibody can be monoclonal or polyclonal and can be prepared by commonly used techniques such as immunization of a host and collection of sera (polyclonal) or by preparing continuous hybrid cell lines and collecting the secreted protein (monoclonal), or by cloning and expressing nucleotide sequences or mutated versions thereof coding at least for the amino acid sequences required for specific binding of natural antibodies.

Polymeric Carriers

The conjugating partners can also include polymers, which in various embodiments can be naturally occurring or synthetic. Examples of polymers include proteins, glycopeptides, polysaccharides such as dextran such as aminodextran or carboxymethyldextran, and bioolymer derivatives of dextran such as dextran sulfate, hydroxyethylstarch, cellulose and cellulose derivatives, including methylcellulose and carboxymethyl cellulose, starch and starch derivatives, inulin, heparin, heparin fragments; synthetic polymers such as polyalkyl glycols (PAG) such as PEG and derivatives thereof, polyoxyethylated polyols (POP) such as polyoxyethylated glycerol (POG), polytrimethylene glycol (PTG), polypropylene glycol (PPG), polyhydroxyethyl methacrylate, polyvinyl alcohol (PVA), polyacrylic acid. polyethyloxazoline, polyacrylamide, polyvinylpyrrolidone (PVP), polyamino acids, polyurethane and polyphosphazene, poly(lactic acid-co-ethylene glycol PLA-PEG, poly(D,L-lactic-co-glycolic acid PLGA, poly(orthoester), Poly(lactide-co-glycolide)-block-poly(ethylene glycols, polyoxyethylated polyols, polyvinylpyrrolidone, polyhydroxyethyl methacrylate, polyvinyl alcohols, and polyurethane ol)-block-poly(lactide-co-glycolide) (PLGA-PEG-PLGA), poly(N-isopropylacrylamide, polyoxyethylated polyols, polyhydroxyethyl methacrylate, N-(2-hydroxypropyl)methacrylamide (HPMA), synthetic copolymers of hydrazone, polyvinyl pyrrolidone, polyvinyl alcohol, polyamino acids, divinylether maleic anhydride, N-(2-Hydroxypropyl)-methacrylamide, polypropylene glycol, polyalkylene glycol and derivatives thereof, copolymers of polyalkylene glycols and derivatives thereof, polyvinyl ethyl ethers, and .alpha.,.beta.-Poly[(2-hydroxyethyl)-DL-aspartamide, poly(N-acryloylmorpholine (PacM). In general, the synthetic polymers can also be linear or branched, substituted or unsubstituted, homopolymeric, or co-polymers of two or more different synthetic monomers.

Pegylation of peptides and proteins can result in enhanced therapeutic properties with retention of biological function. Conjugation with PEGs (or with other polymers, like dextrans), by increasing molecular size, can reduce the processes of renal filtration, immune response, and degradation by proteolytic enzymes, all of which act to enhance stability in vivo. PEG (polyethylene glycol) is a linear strand of repeating monomers, which can be chemically activated at terminal free hydroxyl groups. Such activation can result in reactivity to a number of functional groups, including sulfhydryl and amino groups. To prevent cross-linking, one of the two terminal hydroxyl groups may be capped with a methoxy group (mPEG). PEGs with multiple forks or branches can also be synthesized, allowing for multiple points of attachment for peptides on an individual PEG molecule.

Peptides containing a free sulfhydryl group (as Cysteine, abbreviated Cys using the three-letter amino acid designation) will readily undergo an alkylation reaction with at least one of MPEG modified with maleimide, forming a stable thioester bond. In the case of gastrin, a synthesized gastrin compound with a Cysteine residue introduced in a region of the peptide that is not required for its biological activity (for example, at its N-terminal), can be used.

Peptides containing free amines (as Lysine or N-terminal amino groups) can react with PEGs modified with succinimidyl esters to produce stable amide linkages. Due to the lack of specificity of the chemical reaction, as in the case of gastrin-34, which contains 3 lysine residues, any one, or more, of the lysine residues could react with the modified PEG, resulting in a chemically, and possibly functionally, heterogeneous mixture of conjugated peptides, purification of which may not be trivial. Site-specific PEGylation of a particular lysine residue may be easily attained during peptide synthesis, by introducing a lysine residue in which a PEG is already linked to the ε-amino side chain (as described by Felix (1997)). Felix, A. M. (1997) Site-Specific Poly(ethylene glycol)ylation of Peptides. In "Poly(ethylene glycol). Chemistry and Biological Applications." Harris, J. M. & Zalipsky S. Eds.

The "activated PEG" (or "pegylating agent") is any PEG derivative, which can be used as protein modifier, because it contains a functional group capable of reacting with some functional group in the protein/peptide to produce the PEG-protein/peptide conjugates. Activated PEGs can include alkyating PEGs, acylating PEGs and PEG with an amino acid arm. One can also pegylate at cysteine residue by using PEG maleimide (e.g. mPEG-maleimide-20,000 from Shearwater Corporation, Huntsville, Ala.). Amino PEG can be used to pegylate carboxyl groups. Examples of active PEGS include methoxypolyethylene glycol, diaminomethoxy-polyethylene glycol, methoxypolyethylene glycol-p-nitro-phenylcarbonate, methoxypolyethylene glycol succinimidyl succinate, methoxypolyethylene glycol tresylate, methoxy-polyoxyethylene amine (aminoPEG), methoxypolyoxyethylene-carboxylic acid, monomethoxy-PEG p-nitrophenyl carbonate, N—N'-Carbonyldiimidazole-activated PEGand methoxypolyoxyethyleneimidazole-carbonyl. PEGs of different molecular weights are available commercially. The average molecular weight of the reactant PEG can range from between about 5,000 and about 100,000 daltons. The method of attachment is not critical, but preferably does not alter, or only minimally alters, the activity of the biologically active molecule. A preferred method of attachment is via N-terminal linkage to a polypeptide. See Veronese, Biomaterials 22(5): 405 (2001) for a review of the different activation strategies for PEG. Alternatively PEG can be conjugated to the peptide/protein via glycopegylation by first derivatizing gastrin with sugars molecules prior to conjugation (i.e. glycopegylation approach e.g. using Neose's GlycoPEGylation technology).

Dextran is a naturally occurring polymer that consists of mainly a linear polysaccharide of repeating units of D-glucose linked together in glycosidic bonds. Branch points may be present in a dextran polymer and the branch type and degree of branching vary by species. Dextran can be used here to conjugate to gastrin compounds. The average molecular weight of the soluble dextran can range from between about 10,000 and about 500,000 daltons. Dextran polymer contains adjacent hydroxyl groups on each glucose monomer that can be oxidized by sodium periodate to give a functional aldehyde group that can then react with an amino group. Polyaldehyde dextran can conjugate to amine groups by Schiff base formation followed by reductive amination to create stable linkage, for instance to the epsilon amino group on lysine residue. Dextrans can be carboxymethylated by reaction with monochloroacetic acid to give carboxymethyldextran, which can form dextran-hydrazide on condensation with hydrazine, which reacts with the carbonyl group or aldehyde groups. Sulhydryl reactive dextran derivatives can be prepared through the use of heterobifunctional crosslinking agent containing for instance pyridyldisulfide, maleimide or iodoacetyl groups on one end to direct the conjugation reaction to sulhydryl groups.

Conjugation to Lipophilic Moieties

A lipophilic substituent can be attached to a reactive group of an amino acid at the N-terminal end of the gastrin peptide, or optionally to a reactive group generated via a heterobifunctional or homobifunctinal crosslinker group. For instance, the carboxyl group of the lipophilic substituent can react with the amino group on lysine. For instance, the lipophilic substituents are in particular long-chain groups containing e.g. 8-40 carbon atoms. For instance, the lipophilic substituents can be a straight chain or branched alkyl group, an acyl group of a straight chain or branched fatty acid, an acyl group of a straight chain or branched alkane α,ω-dicarboxylic dicarboxylic acid. For example, lipophilic derivatives of gastrin can be synthesized by chemical attachment to an amino group, for instance, at the N-terminal with various fatty acids including lauric acid (n-dodecanoic acid), myristic acid (n-tetradecanoic acid), palmitic acid (n-hexadecanoic acid), palmitoleic acid (n-hexadecenoic acid), stearic acid (n-octadecanoic acid), oleic acid (n-octadencenoic acid), acetic acid, linoleic acid and arachidonic acid.

Alternatively, a hydrophobic moiety that is conformationally rigid (i.e. presence of a double bond, a triple bond, or a saturated or unsaturated ring) can be attached to the gastrin peptide. For instance, a long chain fatty acids comprising of a carboxyl group can be attached to amino groups found for example on lysine residue.

Bifunctional Crosslinking Agents

Examples of crosslinking agents include but are not limited to the following Amino group directed homobifunctional cross-linking reagents include: Bisimidoesters (Bisimidates), e.g. methyl acetimidate-HCl, dimethyl suberimidate-2HCl; Bis-N-Succinimidyl Derivatives, e.g. bis(sulfosuccinimidyl-suberate (BSSS), succinate bis-(N-hydroxy-succinimide ester); Bifunctional Aryl Halides, e.g. 1,5,-dichloro-2,4-dinitrobenzene; Bifunctional Acylating Agents, such as diisocyanates and diisothiocyanates, e.g. 1,6,-hexamethylene diisocyanate; bifunctional sulfonyl halides, e.g. phenol-2,4,-disulfonyl-chloride; bis-nitrophenol esters, e.g. bis-(p-nitrophenyl ester) of carboxylic acids; and bifunctional acylazides, e.g. tartryl diazide; Dialdehydes, e.g., glutaraldehyde; Diketones, e.g. 2.5-hexanedione; and others such as benzoquinone, 2-iminothiolane, erythreitolbiscarbonate, mucobromic acid, mucochloric acid, ethylchlorofommate, p-nitrophenylchloroformate, succinimidyl 6-hydrazinonicotinate acetone hydrazone and succinimidyl 4-formylbenzoate (for instance the first modifies an amine with a hydrazine linker and the second modifies an amine to an aldehyde linker, which can then be crosslinked together Another group of bifunctional crosslinking agents are the Sulfhydryl group directed homobifunctional crosslinkers, which include: Mercurial Reagent, e.g. 1,4,-bis(bromomercuri)butane; Disulfide Forming Reagents, e.g. polymethylenebis(methanthiosulfonate); Bismaleimides, e.g. N,N'-methylenebismaleimide, Bis(N-maleimidomethyl)ether, bis-maleimidoethane, 1,4-bis-maleimidobutane, 1,4-bis-maleimidyl-2,3-dihydroxybutane, bis-maleimidohexane, 1,8-bis-maleimidotriethyleneglycol. Yet another group are Alkylating Agents such as Bio-haloacetyl derivatives, e.g. 1,3,-dibromoacetone; Di-alkyl halides, e.g. di(2-chloroethyl) sulfide; S-triazines, e.g. 2,4,-dichloro-6-methoxy-s-triazine; Aziridines, e.g. 2,3,4-tri(ethyleneimino)-s-triazine; and Bis-epoxides, e.g. 1,2,3,4-diepoxybutane; and others e.g. divinyl sulfone.

Other group directed homobifunctional crosslinkers are known in the art of chemical cross-linking, such as Carboxyl group directed reagents, e.g. bisdiazohexane; Phenolate and Imidazolyl group directed reagents, e.g. bis-benzidine; Arginine Reagent, e.g. p-phenylenediglyoxal; and others e.g. cis-dichlorodiaminoplatinum(II) (used to crosslink alpha2-macroglobulin with one or more methionine residues at or near the recognition site, may crosslink complementary strands of DNA adipid acid dihydrazide as well as crosslink glycoproteins, acid phosphatase and invertase), N,N'-bis(b-aminoethyl)-tartramide.

Also know in the art are Group selective heterobifunctional crosslinkers, which include: Amino and sulfhydryl group directed bifunctional reagents, e.g., N-succinimidyl 3-(2-pyridyldithio propionate) (SPDP) and its analogs (LC-SPDP, Sulfo-LC-SPDP), Succinimidyloxycarbonyl-α-methyl-α-(2-pyridyldithio)toluene (SMPT) and its analog Sulfosuccinimidyl-6-{α-methyl-α-(2-pyridyldithio)toluamido]hexanoate (Sulfo-LC-SMPT), Succinimidyl-4-(N-maleimidomethyl)cyclohexane-1-carboxylate (SMCC) and its analog, Sulfosuccinidimidyl 4-(N-maleimidomethyl-cyclohexane-1-carboxylate (Sulfo-SMCC), m-Maleimidobenzoyl-N-hydroxy-succinimide ester (MBS) and its analog m-Maleimidobenzoyl-N-hydroxy-sulfosuccinimide ester (Sulfo-MBS), N-succinimidyl(4-iodoacetyl)-aminobenzoate (SIAB) and its analog, Sulfo-suciinimidyl(4-iodoacetyl-aminobenzoate (sulfo-SIAB), Succinimidyl-4-(p-maleimidophenyl)butyrate (SMBP) and its analog, Sulfosuccinimidyl-4(p-maleimidophenylbutyrate (sulfo-SMPB), N-γ-Maleimidobutyryl-oxysuciinimide ester (GMBS) and its analog (Sulfo-GMBS), succinimidyl 6-[(iodoacetyl0)-amino]hexanoate (SIAX) and its analog sucinnimidyl 6-[6-(((iodoacetyl)amino)-hexanoyl]amino]hexanoate (SIAXX), Succinimdl 4-(((iodoacetyl)amino)methyl)-cyclohexane-1-carboxlate (SIAC) and its anlog, suciinimidyl 6-((((4-(iodoacetyl)amino)methyl)-cyclohexane-1-cabornyl)amino) hexanoate (SIACX), N-succinimidyl 4-maleimidobutyrate; Carboxyl and either sulfydryl or amino group directed bifunctional reagents, e.g., p-nitrophenyl diazoacetate; Carbonyl and sulfhydryl group directed bifunctional reagents, e.g. 1-(aminooxy)-4-[(3-nitro-2-pyridyl)dithio)]butane; 4-(-4-N_maleimidophenyl)butyric acid hyrazide hydrochloride (MPBH), 4-(N-Maleimidomethyl)cyclohexane-1-caborxyl-hydrazide ($M_2C_2H$), 3-(2-Pyridyldithio)propionyl hydrazide (PDPH) and others e.g. 2-methyl-N'-benzenesulfonyl-$N^4$-bromoacetylquinonediimide, N-hydroxysuccinimidyl-p-formylbenzoate, methyl-4-(6-formyl-3-azido-phenoxy)butyrimidate HCl, acrolein.

Further included in embodiments of suitable cross-linking agents are the group of Zero-length crosslinking agents, which includes: Carboxyl group activating agents, such as carbodiimides e.g., 1-ethyl-3-(3-dimethylaminopropyl)-carbodiimide hydrochloride (EDC) (activates a carboxyl group than can then crosslink with a NH2 group); isoxazloium derivatives; chloroformates; carbonyldiimidazole; and N-carbalkoxydihydroquinolines; Disulfide forming reagent e.g. cupric di(1,10-phenanthroline); Enzymes e.g. transglutaminase, peroxidase (between lysine residues), xanthine oxidase (forms disulfide bonds); and others e.g. pyrroloquinolinequinone (converts lysines to semi-aldehydes that can then react with other lysine residues).

Pharmaceutical Compositions

The present invention in various embodiments provides pharmaceutical compositions comprising a therapeutically effective amount of a combination of the gastrin compound alone or the combination of a FACGINT, or an hypoglycemic agent with a gastrin compound. All of the pharmaceutical compositions described herein can be formulated with or without an agent for immune suppression, and with or without components or devices for sustained release, for delivery locally or systemically. A pharmaceutically acceptable carrier or excipient can be added. Such a carrier includes but is not limited to saline, buffered saline, dextrose, water, glycerol, ethanol, and combinations thereof. The formulation should suit the mode of administration. An "effective amount" as the term is used herein is an amount of a therapeutic agent or combination of agents sufficient to achieve a recognized medical endpoint, in this case, remediation of a symptom of diabetes. The effective amount can be determined empirically by a skilled artisan according to established methods of measurement of relevant parameters, as described herein.

The compositions herein can further comprise wetting or emulsifying agents, or pH buffering agents. The composition can be a liquid solution, suspension, emulsion, tablet, pill, capsule, sustained release formulation, or powder. The compositions can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Various delivery systems are known and can be used to administer a composition of the invention, e.g., encapsulation in liposomes, microparticles, microcapsules and the like.

In an exemplary embodiment, a composition herein is formulated in accordance with routine procedures as a pharmaceutical composition adapted, for example, for subcutaneous administration to human beings. Typically, compositions for subcutaneous administration are solutions in sterile isotonic aqueous buffer. Where necessary, the composition may also include a solubilizing agent and a local anesthetic to ameliorate pain at the site of the injection. Generally, the ingredients are provided either separately or mixed together in unit dosage form, for example, as a dry, lyophilized powder or water-free concentrate in a hermetically sealed container such as an ampoule or sachette, for example, indicating the quantity of active agent. Where the composition is to be administered by infusion, it can be dispensed with an infusion bottle containing sterile pharmaceutical grade water, buffer, or saline. Where the composition is administered by injection, an ampoule of sterile water or saline for injection can be provided so that the ingredients may be mixed prior to administration. The compositions herein can in various components thereof be formulated as suppositories, which contain active ingredient in the range of about 0.5% to about 10% by weight; oral formulations preferably contain about 10% to about 95% active ingredient by weight. A daily dose is administered as a single dose, or is divided into a plurality of smaller fractional doses, to be administered several times during the day.

As used herein, a dosing schedule refers to a protocol for administering any of the compositions comprising for instance a modified gastrin compound as provided herein, or the modified gastrin in combination with a FACGINT or with a hypoglycemic agent and/or with an immunosuppressant, each in an effective dose, administered simultaneously or within a particular interval of each other, for example, within one day of each other, or as a combined preparation, or separately, and includes the amount of the composition delivered per unit time such as per day, and the duration or period of time over which each composition is administered.

In one aspect, the invention provides a method for preventing or treating diabetes, the method comprising administering to a mammal in need thereof composition of gastrin compound alone or in combination with a FACGINT a FACGINT or with a hypoglycemic agent and/or with an immunosuppressant, each in an amount sufficient to increase the number of pancreatic insulin secreting β cells in the mammal; and determining the amount of islet neogenesis, thereby treating or preventing the diabetes. Determining the amount of islet neogenesis is measuring a parameter selected from the group of: blood glucose, serum glucose, blood glycosylated hemoglobin, pancreatic β cell mass, serum insulin, and pancreatic insulin content. Administering the composition described herein reduces blood glucose compared to blood glucose assayed prior to administering the composition, for example, administering the composition reduces blood glucose by about 50%, or by about 70%, compared to blood glucose assayed prior to administering the composition. Glycosylated hemoglobin concentration is reduced compared to glycosylated hemoglobin concentration in the mammal assayed prior to administering the composition. Serum insulin concentration is increased compared to serum insulin concentration in the mammal assayed prior to administering the composition. Pancreatic insulin concentration is increased compared to pancreatic insulin concentration in the mammal assayed prior to administering the composition.

The compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the therapeutic of the invention which will be effective in the treatment of a particular disorder or condition will depend on the nature of the disorder or condition, and can be determined by standard clinical techniques. The precise dose to be employed in the formulation will also depend on the route of administration, and the seriousness of the disease or disorder, and should be decided according to the judgment of the practitioner and each patient's circumstances. Routine determinations of blood levels of insulin or C peptide, and of fasting levels of glucose or glucose challenges, are determined by one of ordinary skill in the art. Effective doses may be extrapolated from dose-response curves derived from in vitro or animal model test systems, by one of ordinary skill in the art of pharmacology. Dosages of the compositions to be administered to a subject are adjusted for known variations from species to species using standard data encompassing criteria for absorption, distribution, half-life kinetics in circulation, metabolism, excretion, and toxicology of the receptor ligands of the embodiments herein. Suitable dosage ranges for administration are generally about 0.01 micrograms to about 10,000 micrograms of each active compound per kilogram body weight per day, for example, about 0.01 micrograms to about 1 microgram/kg, about 0.1 micrograms/kg to about 10 micrograms/kg, about 1 microgram/kg to about 500 micrograms/kg, or about 10 micrograms/kg to about 10 mg/kg of body weight per day. Suitable dosage ranges for administration are thus generally about 0.01 micrograms/kg body weight/day to about 10 mg/kg body weight/day.

The invention in other embodiments provides a pharmaceutical pack or kit comprising one or more containers filled with one or more of the ingredients of the pharmaceutical compositions of the invention. In such a pack or kit can be found a container having a unit dosage of the extended use gastrin compound. Associated with such container(s) can be various written materials such as instructions for use, or a notice in the form prescribed by a governmental agency regulating the manufacture, use or sale of pharmaceuticals or biological products, which notice reflects approval by the agency of manufacture, use or sale for human administration.

Unless otherwise defined, all technical and scientific terms herein have the same meaning as commonly understood by one of ordinary skill in the art to which this invention pertains. Methods and materials similar or equivalent to those described herein can be used in the practice of the present invention. The invention in various embodiments now having been fully described, additional embodiments are exemplified by the following Examples and claims, which are not intended to be construed as further limiting. The contents of all cited references are hereby incorporated by reference in their entirety herein.

EXAMPLES

Example 1

Pharmacokinetic Example of Unmodified Gastrin Following Administration by Intravenous Injection to Male Cynomolgus Monkeys This example was conducted to assess the pharmacokinetic (PK) profile of unmodified gastrin (referred to herein as compound B; see Table 3) following administration by a single intravenous injection to male cynomolgus monkeys. The 17 amino acid gastrin analog used has a single amino acid change at position 15, where methionine has been substituted by leucine. While compound B thus is not identical to naturally occurring gastrin, all available evidence indicates that it is functionally equivalent to gastrin.

Terms associated with PK analysis terms are defined as follows:

$C_{max}$—The maximum observed plasma concentration $t_{max}$—The time to maximum concentration AUC—Area under the curve, a measure of total exposure to a drug over a period of time Plasma $t_{1/2}$—A measure of how long a drug stays in the blood. the time it takes for the plasma concentration to fall 50%

Administration of Gastrin

Male animals were used in the example. Each animal received gastrin by intravenous administration (3 µg/kg, 10 µg/kg and 30 µg/kg). The dosing solutions for intravenous injection were administered as a single bolus dose via the saphenous vein at a dose volume of 1 mL/kg. A 0.2 mL saline flush was administered following dosing in order to ensure administration of the complete dose volume. The actual volume administered to each animal was based on the animal's most recent body weight.

Blood Collection

Serial blood samples (approximately 0.5 ml per time point) were collected via the brachial or femoral vein at the following time points: 0 (pre-dose), 1, 3, 5, 10, 15, 30 minutes, 1, 2, and 4 hours post dose.

Each sample was collected into a tube containing EDTA and kept on wet ice pending centrifugation. The samples were centrifuged under refrigeration for a minimum of 10 minutes at 1,500 g (RCF) and the resultant plasma was transferred into duplicate tubes and placed on dry ice. All samples were stored frozen for PK analysis as described below.

Assay for Gastrin Levels

Gastrin in plasma samples was measured with a well established competitive radioimmunoassay for the quantitative determination of gastrin (Russell et al., Postgraduate Medical Journal 52:645, 1976). The antibody used in the assay was raised in rabbits against synthetic human gastrin I conjugated with carbodiimide to bovine serum albumin. The antigen was labeled with $^{125}$I and the presence of the antigen:antibody reactions were detected using a gamma counter.

Pharmacokinetics Analysis

To calculate pharmacokinetic parameters, blood levels of gastrin at each time point for every animal were entered in to Graphpad Prism 3.0 (GraphPad Software, San Diego, Calif., USA, www.graphpad.com).

TABLE 2

Summary of mean PK parameters for gastrin in primates after intravenous injection

| Dose COMPOUND B (µg/kg) | t ½ (min) | Cmax (pg/ml) | Tmax (min) | AUC (ng · ml/min) |
|---|---|---|---|---|
| 3 | 5 | 27000 | 2 | 251 |
| 10 | 4 | 127487 | 1 | 939 |
| 30 | 5 | 267625 | 1 | 2526 |

Data from Table 2 demonstrated the relatively short plasma t½ of COMPOUND B which averages around 4-5 minutes for each of the three dose groups. COMPOUND B appeared to be rapidly cleared from the bloodstream of primates after a single bolus administration. With increasing intravenous dose of COMPOUND B, an increasing values of $C_{max}$ and AUC were observed, however increasing the dose did not appear to affect the value of t½. These data show that administering greater amounts of COMPOUND B does not enhance short lifetime of this peptide in circulation. In summary these data demonstrate that gastrin is cleared from the blood stream within minutes. Thus, the presence of biologically active compound in the serum is limited by the rapid clearance of gastrin from the serum.

Example 2

Effect of Unmodified Gastrin on Fasting Blood Glucose Levels and Pancreatic Insulin Content in NOD Mice with Recent Onset Diabetes Non-obese diabetic (NOD) female mice were monitored for diabetes development as determined by a fasting blood glucose (FBG) level of >6.6 mmol/l. After diabetes onset, mice were treated with (i) vehicle (n=4); or, (ii) gastrin (compound B as listed in Table 3) in the amount of 3 µg/kg/day, given i.p. once daily (n=5) for 14 days. Mice did not receive insulin-replacement treatment. Fasting blood glucose levels and pancreatic insulin content were assessed for the two treatment groups at both day 0 and day 35 (21 days after cessation of treatment).

FIG. 1 shows that in the vehicle-treated control animals, fasting blood glucose levels (FBG) were doubled after 35 days. In contrast, treatment with gastrin prevented some of the increase in glucose levels from rising in the diabetic NOD mice, however, the FBG levels remained significantly higher than that observed in normal mice (~3-7 mM). These data show that, in order to reduce blood glucose to normal levels, one may require to increase the efficacy of gastrin.

Figure 2:
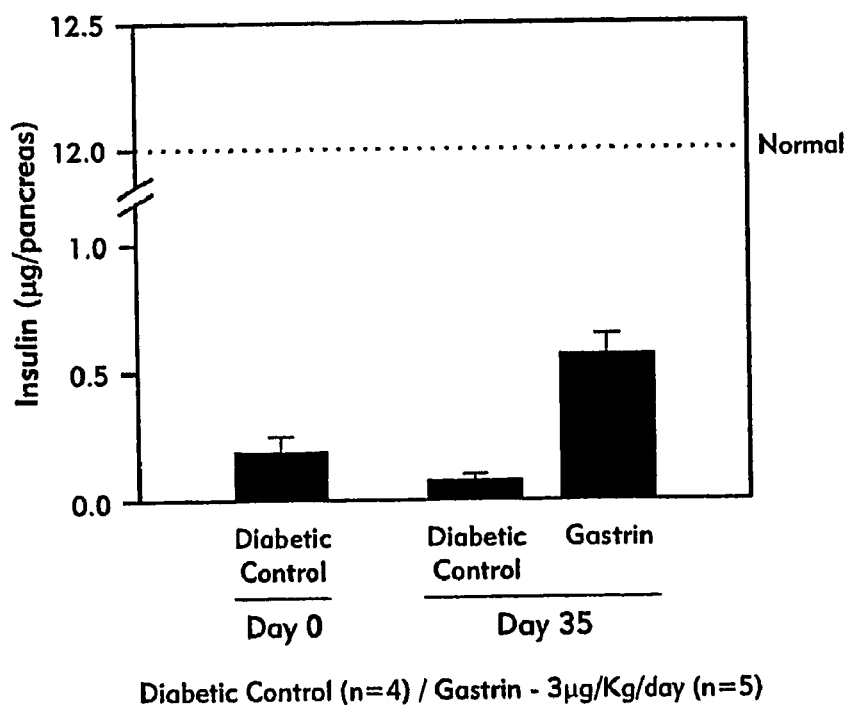
FIG. 2 shows the effect of unmodified gastrin on pancreatic insulin levels of NOD mice with recent onset diabetes after a 14 day treatment

Pancreatic insulin levels for vehicle-treated groups decreased at day 35 due to destruction of beta-cells, whereas animals treated with gastrin exhibited significantly elevated levels of pancreatic insulin levels in comparison with pre-treatment values. See FIG. 2. However, the increase of pancreatic insulin levels after treatment of COMPOUND B to about 0.6 ug of insulin/pancreas is still significantly lower than that of normal mice (~12 ug/pancreas). These data together with the pharmacokinetics analysis in Example I suggest that the efficacy of treating diabetic NOD mice using unmodified gastrin may be limited by the relatively short half life of plasma gastrin (5 mins). Thus, the use of a longer acting gastrin may be more efficacious in stimulating islet cell neogenesis, increasing pancreatic insulin and preventing diabetes progression in NOD mice.

Example 3

Peptide Synthesis of Gastrin Peptides

Gastrin peptides may be readily synthesized by anyone with ordinary skills in the art, using standard techniques for solid phase peptide synthesis, for example as described by Steward, J. M. and Young, J. D. (1984) in "Solid Phase Peptide Synthesis", $2^{nd}$ ed., Pierce Chemical Company. Purification of gastrin peptides may be performed using standard techniques, for example using reverse phase HPLC with a volatile binary gradient system consisting of 0.1% TFA in $H_2O$ and 0.1% TFA in acetonitrile. Monitoring elution by UV absorbance allows for collection of purified peptide, which is then lyophilized to dryness and subsequently dissolved for administration and testing, or for further conjugation reactions where required.

Gastrin synthetic peptides may be synthesized containing any consecutive portion of residues 1-28 in addition to residues 29-34 of SEQ ID NO: 1 or 2 or containing any consecutive portion of residues 1-11 in addition to residues 12-17 of SEQ ID NO: 3 or 4. Additionally, gastrin peptides may be synthesized with a spacer region at the N-terminal end comprised of small neutral amino acid residues such as Gly and Ala Gastrin synthetic peptides, either with or without a spacer region, may also be synthesized with an N-terminal Cys residue.

A summary of some gastrin peptides which are synthesized for use in gastrin compositions herein, are listed in Table 3 (compounds A through H), and include "Big" Gastrin-34 (A), "Little" or "Small" Gastrin-17 (B), and Gastrin-13 (C).

TABLE 3

Summary of gastrin compositions and their components

| Compound | Polymer | N-terminal Cys residue | Linker | Gastrin Peptide | Residues from SEQ ID NO: |
|---|---|---|---|---|---|
| A | No | No | No | 1-34 | 2 |
| B | No | No | No | 1-17 | 4 |
| C | No | No | No | 5-17 | 4 |
| D | No | Yes | No | 2-34 | 2 |
| E | No | Yes | No | 2-17 | 4 |

TABLE 3-continued

Summary of gastrin compositions and their components

| Compound | Polymer | N-terminal Cys residue | Linker | Gastrin Peptide | Residues from SEQ ID NO: |
|---|---|---|---|---|---|
| F | No | Yes | No | 5-17 | 4 |
| G | No | Yes | $(GA)_5$ | 2-17 | 4 |
| H | No | Yes | $(GA)_5$ | 5-17 | 4 |
| I | PEG | Yes | No | 2-34 | 2 |
| J | PEG | Yes | No | 2-17 | 4 |
| K | PEG | Yes | No | 5-17 | 4 |
| L | PEG | Yes | $(GA)_5$ | 2-17 | 4 |
| M | PEG | Yes | $(GA)_5$ | 5-17 | 4 |
| N | HSA | Yes | No | 2-34 | 2 |
| O | HSA | Yes | No | 2-17 | 4 |
| P | HSA | Yes | No | 5-17 | 4 |
| Q | HSA | Yes | $(GA)_5$ | 2-17 | 4 |
| R | HSA | Yes | $(GA)_5$ | 5-17 | 4 |

PEG is poly(ethylene glycol)-20,000;
HSA is human serum albumin; $(GA)_5$ is Gly-Ala-Gly-Ala-Gly-Ala-Gly-Ala-Gly-Ala spacer.

Example 4

Conjugation of Gastrin with PEG-20,000

Gastrin peptides modified with Cys at the N-terminal (compounds D, E, F, G, and H in Table 3) are incubated for about 30 minutes at near neutral conditions (buffered at pH 6.5-7.5) with a molar excess of tris[2-carboxyethyl]phosphine hydrochloride (TCEP; a reducing agent which has no reactivity with maleimide moieties) to ensure that the Cys residue is in the reduced state and available for reaction.

A molar excess of mPEG-maleimide-20,000 (average MW 20,000; obtained from Shearwater Corporation, Huntsville Ala., USA) is added gradually with mixing to allow dissolution, and when fully dissolved, the solution is mixed for an additional 1 to 4 hours to allow for completion of the conjugation reaction. Purification of the conjugate may be performed using an anion-exchanger, for example Q-Sepharose at neutral pH, to which both the conjugate and any free unreacted gastrin binds tightly, since the theoretical isoelectric point (pI) for gastrin is 3.4, whereas the neutral unreacted mPEG-malemide does not bind. For further purification, the conjugate is readily separated from unreacted gastrin based on the large difference in their molecular weights using size exclusion chromatography, for example using Sephadex G-50, using a buffer suitable for therapeutic use such as PBS.

These reactions result in the production of compounds I, J, K, L and M in Table 3. Success of conjugation reactions is verified using the Biuret reaction for peptide content, a colorimetric procedure for PEG content (Habeeb, A.F.S.A. (1966) Anal. Biochem. 14: 328-336), and electrospray mass spectrometry to determine the total MW of the conjugate.

Example 5

Conjugation with Human Serum Albumin

Serum albumin contains a single accessible, reduced Cysteine residue (Cys-34), which is the most reactive thiol group among human plasma proteins (Pedersen et al (1980) Eur. J. Biochem. 106: 291-295). This property allows specific conjugation of ligands, including peptides, to serum albumin.

Human serum albumin is incubated for about 30 minutes at near neutral conditions (buffered at pH 6.5-7.5) with a molar excess of tris[2-carboxyethyl]phosphine hydrochloride (TCEP; a reducing agent which has no reactivity with maleimide moieties) to ensure that Cys-34 residue is in the reduced state and available for reaction. A molar excess of bis-maleimidoethane (a homo-bifunctional cross-linking agent having a short spacer, and reactivity towards sulfhydryl groups) is added to activate Cys-34. In separate reactions, gastrin peptides modified with Cys at the N-terminal (compounds D, E, F, G, and H in Table 3) are added and the resulting solution is mixed for an additional 1 to 4 hours to allow for completion of the conjugation reaction. The conjugate is readily separated from unreacted gastrin (and any gastrin dimers formed) based on the large difference in their molecular weights using size exclusion chromatography, for example using a buffer suitable for therapeutic use, such as PBS. Unreacted HSA was not further separated from HSA conjugated with Gastrin peptides.

These reactions result in the production of compounds N, O, P, Q and R in Table 3. Success of conjugation reactions is verified using electrospray mass spectrometry to measure total MW of conjugate.

Example 6

Pharmacokinetic Comparison Between Unmodified and Modified Gastrin Compounds Following Administration by Intravenous Injection to Wistar Rats This example was conducted to assess the pharmacokinetic profile of unmodified and modified gastrin derivatives/conjugates following iv injection in Wistar rats.

Administration of Gastrin

Rats (groups of three animals) receive the various test compounds as synthesized in Example 3 at the dose level of 10 µg/kg of gastrin equivalent by iv administration. The following test compounds are used are all of the compounds listed in Table 3 above. Please refer to Table 3 for more details.

Blood Collection

Serial blood samples (approximately 0.4 ml per time point) were collected at the following time points: 5, 60, 180, 480 minutes after the injection all animals. At each time point, blood was taken from at 3 animals per group.

Each sample was collected into a tube containing EDTA and kept on wet ice pending centrifugation. The samples were centrifuged under refrigeration for a minimum of 10 minutes at 1,500 g (RCF) and the resultant plasma transferred into duplicate tubes and placed on dry ice. All samples were stored frozen for PK analysis.

Assay for Gastrin Levels

Human Gastrin 1 (G-17) Immunoassay Kit from R&D systems, catalog number DE3400 was used to measure plasma COMPOUND B levels using the ELISA method. This assay is based on the competitive binding technique in which Gastrin I present in a sample competes with a fixed amount of alkaline phosphatase-labeled Gastrin I for sites on a rabbit polyclonal antibody. During the incubation, the antibody becomes bound to the goat anti-rabbit antibody coated onto the microplate. Following a wash to remove excess conjugate and unbound sample, a substrate solution is added to the wells to determine the bound enzyme activity. Immediately following color development, the absorbance is read at 405 nm. The intensity of the color is inversely proportional to the concentration of Gastrin I in the sample.

Pharmacokinetics Analysis

Plasma concentration of gastrin (COMPOUND B) and its different derivatives/conjugates were analyzed using the PK Functions for Microsoft® Excel (Usansky J I, Desai A, Tang-Liu D, Department of Pharmacokinetics and Drug Metabolism, Irvine, Calif.). To assess the PK profiles, various test compounds and the following PK values were calculated: $C_{max}$, $t_{max}$, AUC and $t_{1/2}$.

Since gastrins (e.g. COMPOUND B) are naturally occurring at detectable levels in blood, baseline values obtained before dosing were subtracted from the plasma levels obtained after COMPOUND B administration. Data are expressed as mean±SD.

The data show that modified gastrin compounds with cysteine as functional groups on the N-terminus), or modified gastrin compounds conjugated to PEG or HSA on the N-terminus had significantly longer half lives compared to native gastrin. The modified gastrin compounds/conjugates are present in serum at higher concentrations for longer periods of time compared to the administration of native gastrin 17 or gastrin 34. These data also demonstrate the AUCs also increase with the chemical modification of the gastrin molecules. It is envisioned that the modified gastrin derivatives/conjugates provide the highest concentrations for the longest period of time will have the greatest potential for the efficacy required for islet cell neogenesis and regulation of glucose levels in diabetic animals.

Example 7

Comparison of Modified Gastrin-Compounds and Unmodified Gastrin in Preventing Diabetes Progression in NOD Mice with Recent Onset Diabetes In this example, the effect of treatment by unmodified gastrin and modified gastrin compounds/conjugates were examined in NOD mice with recent onset diabetes, to determine whether administration of the various modified gastrin derivatives/conjugates would be more effective in preventing severe hyperglycemia as well as increase pancreatic insulin content in NOD mice with recent-onset diabetes as compared to unmodified gastric. Modified gastrin compounds/conjugates used are as follows (Refer to Table 3 for more details): Compound B, which is gastrin prepared as synthetic human gastrin I having 17 amino acid residues with a Leu residue at amino acid position 15, Compound E, Compound G, Compound J, Compound L, Compound O and Compound Q.

Non-obese diabetic (NOD) female mice, ages 12-14 weeks, are monitored for development of onset of diabetes (fasting blood glucose >8.0 to 15 mmol/l), and within 48 hours after onset of symptoms, the different groups of mice are each treated with 3 or 10 µg/kg/day of Gastrin equivalent, each treatment administered via the intraperitoneal route daily.

Therapy is administered for 14 days. Animals are monitored weekly for fasting blood glucose (FBG) levels. FBG levels are measured at about 12 hours after food had been withdrawn, and 24 hours after the last peptide or vehicle injection. Upon cessation of therapy, all mice are monitored for FBG levels for the next 4 weeks (weeks 2-6) so as to determine whether prevention of hyperglycemia persisted after termination of therapeutic treatment. At 14 days treatment is stopped.

The protocol includes sampling of these mice for data again at 6 weeks, and blood collected for assay of FBG and plasma C-peptide, and the mice are sacrificed for pancreatic insulin determinations and scoring of islet inflammation (insulitis). From the outset of treatment, mice receive neither insulin-replacement treatment nor immunosuppression. The following parameters are assessed: survival rates, pancreatic insulin levels, presence of islet inflammation and fasting blood glucose levels.

The data demonstrate that modified gastrin derivatives/conjugates with a longer half life and AUCs were more effective in preventing hyperglycemia in diabetic NOD mice. In some cases, the modified gastrin compounds/conjugates completely reverse the glucose levels to normal levels, indicating the stimulation of significant levels of islet neogenesis in this model.

Example 8

Comparison of Modified Gastrin Compounds/Conjugates and Unmodified Gastrin in Combination with GLP-1 in Preventing Diabetes Progression in Nod Mice with Recent Onset Diabetes In this example, the effect of treatment by a combination of GLP-1 and unmodified gastrin and GLP-1 and modified gastrin compounds/conjugates were examined in NOD mice with recent onset diabetes, to determine whether administration of both GLP-1 and gastrin would prevent severe hyperglycemia as well as increase pancreatic insulin content in NOD mice with recent-onset diabetes. The GLP-1 used was GLP-1 which is the biologically active fragment of human/mouse GLP-1 (having residues at positions 7-36 compared to the precursor from which the fragment is processed; obtained from Bachem H6795). Modified gastrin compounds/conjugates used are as follows: Compound B-COMPOUND B-gastrin as synthetic human gastrin I having 17 amino acid residues with a Leu residue at amino acid position 15, Compound E, Compound Q.

Non-obese diabetic (NOD) female mice, ages 12-14 weeks, were monitored for development of onset of diabetes (fasting blood glucose >8.0 to 15 mmol/l), and within 48 hours after onset of symptoms, four groups of mice were each treated as follows: one group was treated with vehicle only, and the other group was administered 100 µg/kg/day of GLP-1, and the remaining groups were treated with combination of GLP-1 (100 µg/kg/day) and gastrin compound (3 µg/kg/day gastrin equivalent), each treatment administered via the intraperitoneal route daily.

Therapy was administered for 14 days. Animals were monitored weekly for fasting blood glucose (FBG) levels. FBG levels were measured at about 12 hours after food had been withdrawn, and 24 hours after the last peptide or vehicle injection. Upon cessation of therapy, all mice were monitored for FBG levels for the next 4 weeks (weeks 2-6) so as to determine whether prevention of hyperglycemia persisted after termination of therapeutic treatment. At 14 days treatment was stopped.

The protocol includes sampling of these mice for data again at 6 weeks, and blood collected for assay of FBG and plasma C-peptide, and the mice are sacrificed for pancreatic insulin determinations and scoring of islet inflammation (insulitis). From the outset of treatment, mice received neither insulin-replacement treatment nor immunosuppression. The following parameters are assessed: survival rates, pancreatic insulin levels, presence of islet inflammation and fasting blood glucose levels.

The data demonstrate that GLP-1 in combination of modified gastrin compounds/conjugates (Compound E or Q) with longer half lives were more effecting in reducing blood glucose levels in diabetic animals compare to GLP-1 with native gastrin (Compound B). These data support the use of longer lasting modified gastrin compounds/conjugates with GLP-1 or other growth factors.

What is claimed is:

1. A gastrin compound which comprises an amino acid sequence comprising from the amino acid terminus Z—$Y_m$—$X_n$-$AA_1$-$AA_2$-$AA_3$-$AA_4$-$AA_5$-$AA_6$, wherein Z is human serum albumin; $X_n$ is Gly-Pro-Trp-Leu-Glu-Glu-Glu-Glu-Glu-Ala (SEQ ID NO:9). $AA_1$-$AA_2$-$AA_3$-$AA_4$-$AA_5$-$AA_6$ is Tyr-Gly-Trp-Leu-Asp-Phe (SEQ ID NO:6) or Tyr-Gly-Trp-Met-Asp-Phe (SEQ ID NO:5), $Y_m$ is an optional spacer region comprising m amino acid residues of a small neutral amino acid, and wherein there is a cysteine residue at the amino terminus of Y wherein m is 1 or greater, or at the amino terminus of X when m is 0, providing that the gastrin compound binds a gastrin/$CCK_B$ receptor.

2. A gastrin compound according to claim 1 which comprises $Y_m$ wherein m is 5 and Y is (Gly-Ala).

3. A gastrin compound according to claim 1 wherein m is 0.

4. A gastrin compound according to claim 1 wherein $AA_1$-$AA_2$-$AA_3$-$AA_4$-$AA_5$-$AA_6$ is Tyr-Gly-Trp-Leu-Asp-Phe (SEQ ID NO:6).

5. A gastrin compound according to claim 1 wherein $AA_1$-$AA_2$-$AA_3$-$AA_4$-$AA_5$-$AA_6$ is Tyr-Gly-Trp-Met-Asp-Phe (SEQ ID NO:5).

6. A gastrin compound according to claim 1 wherein said gastrin has extended activity upon administration to a subject in comparison with native gastrin.

7. The gastrin compound of claim 1 wherein $Y_m$ is a spacer region comprising m amino acid residues of a small neutral amino acid.

8. A pharmaceutical composition for use in the treatment of diabetes comprising a gastrin compound according to claim 1 and a pharmaceutically acceptable carrier or excipient.

9. A pharmaceutical composition for use in the treatment of diabetes comprising a gastrin compound according to claim 2 and a pharmaceutically acceptable carrier or excipient.

10. A pharmaceutical composition for use in the treatment of diabetes comprising a gastrin compound according to claim 3 and a pharmaceutically acceptable carrier or excipient.

11. A pharmaceutical composition comprising the gastrin compound of wherein said gastrin has extended activity upon administration to a subject in comparison with native gastrin.

12. A pharmaceutical composition comprising the gastrin compound of wherein said gastrin prevents severe hypoglycemia or increases pancreatic insulin content upon administration to a subject.

13. The gastrin compound of claim 4 wherein $Y_m$ is alternately glycine and alanine amino acids.

14. A pharmaceutical composition comprising a gastrin compound according to claim 4 and a pharmaceutically acceptable carrier or excipient.

15. A pharmaceutical composition comprising a gastrin compound according to claim 5 and a pharmaceutically acceptable carrier or excipient.

* * * * *

UNITED STATES PATENT AND TRADEMARK OFFICE
CERTIFICATE OF CORRECTION

| | | |
|---|---|---|
| PATENT NO. | : 7,803,766 B2 | Page 1 of 1 |
| APPLICATION NO. | : 11/701196 | |
| DATED | : September 28, 2010 | |
| INVENTOR(S) | : Antonio Cruz | |

It is certified that error appears in the above-identified patent and that said Letters Patent is hereby corrected as shown below:

The claims:

Column 39, line 15, claim 11, the phrase "compound of wherein said gastrin has extended activity upon" should read -- compound of claim 3 wherein said gastrin has extended activity upon --.

Column 40, line 2-3, claim 12, the phrase "compound of wherein said gastrin prevents severe hypoglycemia" should read -- compound of claim 3 wherein said gastrin prevents severe hypoglycemia --.

Signed and Sealed this
Twenty-eighth Day of December, 2010

David J. Kappos
*Director of the United States Patent and Trademark Office*

SEQUENCE LISTING

```
<160> NUMBER OF SEQ ID NOS: 9

<210> SEQ ID NO 1
<211> LENGTH: 34
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: Wherein X at position 1 is pyroglutamate
<220> FEATURE:
<221> NAME/KEY: MOD_RES
<222> LOCATION: (34)..(34)
<223> OTHER INFORMATION: Amidation

<400> SEQUENCE: 1

Xaa Leu Gly Pro Gln Gly Pro Pro His Leu Val Ala Asp Pro Ser Lys
1               5                   10                  15

Lys Gln Gly Pro Trp Leu Glu Glu Glu Glu Glu Ala Tyr Gly Trp Met
            20                  25                  30

Asp Phe

<210> SEQ ID NO 2
<211> LENGTH: 34
<212> TYPE: PRT
```

<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: Wherein X at position 1 is pyroglutamate
<220> FEATURE:
<221> NAME/KEY: MOD_RES
<222> LOCATION: (34)..(34)
<223> OTHER INFORMATION: Amidation

<400> SEQUENCE: 2

```
Xaa Leu Gly Pro Gln Gly Pro Pro His Leu Val Ala Asp Pro Ser Lys
1               5                   10                  15

Lys Gln Gly Pro Trp Leu Glu Glu Glu Glu Ala Tyr Gly Trp Leu
            20                  25                  30

Asp Phe
```

<210> SEQ ID NO 3
<211> LENGTH: 17
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: Wherein X at position 1 is pyroglutamate
<220> FEATURE:
<221> NAME/KEY: MOD_RES
<222> LOCATION: (17)..(17)
<223> OTHER INFORMATION: Amidation

<400> SEQUENCE: 3

```
Xaa Gly Pro Trp Leu Glu Glu Glu Glu Glu Ala Tyr Gly Trp Met Asp
1               5                   10                  15

Phe
```

<210> SEQ ID NO 4
<211> LENGTH: 17
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: Wherein X at position 1 is pyroglutamate
<220> FEATURE:
<221> NAME/KEY: MOD_RES
<222> LOCATION: (17)..(17)
<223> OTHER INFORMATION: Amidation

<400> SEQUENCE: 4

```
Xaa Gly Pro Trp Leu Glu Glu Glu Glu Glu Ala Tyr Gly Trp Leu Asp
1               5                   10                  15

Phe
```

<210> SEQ ID NO 5
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 5

Tyr Gly Trp Met Asp Phe

```
<210> SEQ ID NO 6
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 6

Tyr Gly Trp Leu Asp Phe
1               5

<210> SEQ ID NO 7
<211> LENGTH: 4
<212> TYPE: PRT
<213> ORGANISM: Artificial Sequence
<220> FEATURE:
<223> OTHER INFORMATION: General gastrin/CCK receptor ligands carboxy
      terminal amino acid sequence
<220> FEATURE:
<221> NAME/KEY: MOD_RES
<222> LOCATION: (4)..(4)
<223> OTHER INFORMATION: Amidation

<400> SEQUENCE: 7

Trp Met Asp Phe
1

<210> SEQ ID NO 8
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 8

Gly Ala Gly Ala Gly Ala Gly Ala Gly Ala
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 9

Gly Pro Trp Leu Glu Glu Glu Glu Glu Ala
1               5                   10
```